United States Patent
Bigi et al.

(10) Patent No.: US 11,976,017 B2
(45) Date of Patent: May 7, 2024

(54) PROCESSES FOR PREPARING ISOPRENE AND MONO-OLEFINS COMPRISING AT LEAST SIX CARBON ATOMS

(71) Applicant: Dow Technology Investments LLC, Midland, MI (US)

(72) Inventors: Marinus A. Bigi, Pearland, TX (US); Michael A. Brammer, Lake Jackson, TX (US); Glenn A. Miller, South Charleston, WV (US); Amarnath Singh, Pearland, TX (US)

(73) Assignee: Dow Technology Investments LLC, Midland, MI (US)

( * ) Notice: Subject to any disclaimer, the term of this patent is extended or adjusted under 35 U.S.C. 154(b) by 140 days.

(21) Appl. No.: 17/755,724

(22) PCT Filed: Nov. 11, 2020

(86) PCT No.: PCT/US2020/059930
§ 371 (c)(1),
(2) Date: May 6, 2022

(87) PCT Pub. No.: WO2021/126421
PCT Pub. Date: Jun. 24, 2021

(65) Prior Publication Data
US 2022/0402835 A1    Dec. 22, 2022

Related U.S. Application Data

(60) Provisional application No. 62/950,737, filed on Dec. 19, 2019.

(51) Int. Cl.
*C07C 1/24*    (2006.01)
(52) U.S. Cl.
CPC ...................................... *C07C 1/24* (2013.01)
(58) Field of Classification Search
CPC ......... C07C 1/24; C07C 29/141; C07C 45/50; C07C 45/82; Y02P 20/582
See application file for complete search history.

(56) References Cited

U.S. PATENT DOCUMENTS

| | | | |
|---|---|---|---|
| 4,547,614 A * | 10/1985 | Vavere | C07C 1/24 585/606 |
| 4,560,822 A | 12/1985 | Hoelderich et al. | |
| 4,587,372 A | 5/1986 | Hsu | |
| 4,665,266 A | 5/1987 | Hsu et al. | |
| 4,734,538 A | 3/1988 | O'Connor et al. | |
| 4,762,817 A | 8/1988 | Logsdon et al. | |
| 4,777,320 A | 10/1988 | Alvila et al. | |
| 4,876,402 A | 10/1989 | Logsdon et al. | |
| 4,960,960 A | 10/1990 | Harrison et al. | |
| 5,093,535 A | 3/1992 | Harrison et al. | |
| 6,765,119 B2 | 7/2004 | Hoffmann et al. | |
| 6,982,355 B2 | 1/2006 | Abazajian | |
| 7,863,487 B2 | 1/2011 | Eisenschmid et al. | |
| 8,507,731 B2 | 8/2013 | Brammer | |
| 8,598,389 B2 | 12/2013 | Eisenschmid et al. | |
| 8,598,390 B2 | 12/2013 | Eisenschmid et al. | |
| 8,664,451 B2 | 3/2014 | Eisenschmid et al. | |
| 8,741,173 B2 | 6/2014 | Brammer et al. | |
| 10,766,833 B2 | 11/2020 | Zhang | |

(Continued)

FOREIGN PATENT DOCUMENTS

| | | |
|---|---|---|
| CN | 106824282 A | 6/2017 |
| EP | 0008767 A1 | 3/1980 |

(Continued)

OTHER PUBLICATIONS

Hutchings, "Dehydration of 2-Methylbutanal and Methyl Isopropyl Ketone to Isoprene Using Boron and Aluminium Phosphate Catalysts", Journal of Catalysis, 1999, vol. 188 (2), pp. 291-299.

Moffat, "2-Methylbutanal as a Probe Molecule and the Production of Isoprene on Stoichiometric and Nonstoichiometric B—P—O Catalysts", Applied Catalysis, 1986, vol. 28 (1-2), pp. 161-168.

Stauffer, "Kinetics of the Catalytic Dehydration of Primary Alcohols", I&EC Fundamentals., 1962, vol. 1, pp. 107-111.

PCT/US2020/059930, International Search Report and Written Opinion dated Feb. 16, 2021.

(Continued)

*Primary Examiner* — Sharon Pregler

(57) ABSTRACT

The present invention relates to processes for preparing isoprene and mono-olefins comprising at least six carbon atoms. In one aspect, a process comprises (a) hydroformylating a mixed C4 olefin stream, wherein the mixed C4 olefin stream comprises 1-butene, 2-butene, and optionally isobutene, with a hydroformylation catalyst, wherein the hydroformylation catalyst comprises rhodium with monodentate organophosphorous ligand and optionally polydentate organophosphorous ligand, to produce a mixture comprising linear and branched C5 aldehydes; (b) separating the branched C5 aldehydes from the linear C5 aldehydes to provide a branched C5 aldehyde stream and a linear C5 aldehyde stream; (c) dehydrating the branched C5 aldehydes in the branched C5 aldehyde stream using a dehydration catalyst to form a stream comprising isoprene; (d) hydrogenating the linear C5 aldehydes in the linear C5 aldehyde stream to form a C5 alcohol stream; (e) dehydrating the C5 alcohols in the C5 alcohol stream with a second dehydration catalyst to form a C5 olefin stream; (f) hydroformylating the C5 olefins in the C5 olefin stream to generate a C6 aldehyde stream; (g) hydrogenating the C6 aldehydes in the C6 aldehyde stream to form a C6 alcohol stream; and (h) dehydrating the C6 alcohols in the C6 alcohol stream with a third dehydration catalyst to form a C6 olefin stream.

15 Claims, No Drawings

(56) References Cited

U.S. PATENT DOCUMENTS

| | | |
|---|---|---|
| 2005/0065389 A1* | 3/2005 | De Bruyn .............. C07C 45/50 585/639 |
| 2006/0173223 A1 | 8/2006 | De Weerd |
| 2007/0004939 A1 | 1/2007 | Volland et al. |
| 2008/0081909 A1 | 4/2008 | Drent et al. |
| 2010/0048959 A1 | 2/2010 | Sigl et al. |
| 2010/0048969 A1 | 2/2010 | Lauritzen et al. |
| 2010/0069680 A1 | 3/2010 | Eisenschmid et al. |
| 2012/0253081 A1 | 10/2012 | Eisenschmid et al. |
| 2013/0204024 A1 | 8/2013 | Brammer et al. |
| 2015/0336861 A1 | 11/2015 | Geilen et al. |
| 2018/0072647 A1 | 3/2018 | Stochniol et al. |

FOREIGN PATENT DOCUMENTS

| | | |
|---|---|---|
| EP | 0080449 | 6/1983 |
| EP | 0080449 A1 | 6/1983 |
| EP | 0219042 A2 | 4/1987 |
| EP | 0272662 A2 | 6/1988 |
| GB | 2227250 A | 7/1990 |
| WO | 2003/024910 A1 | 3/2003 |
| WO | 2004078336 A2 | 9/2004 |
| WO | 2010138435 | 12/2010 |
| WO | 2010138435 A1 | 12/2010 |
| WO | 2011/087688 A1 | 7/2011 |
| WO | 2011/087690 A1 | 7/2011 |
| WO | 2011/087696 A1 | 7/2011 |
| WO | 2015/094781 A1 | 6/2015 |

OTHER PUBLICATIONS

PCT/US2020/059930, International Preliminary Report on Patentability dated May 17, 2022.

* cited by examiner

PROCESSES FOR PREPARING ISOPRENE AND MONO-OLEFINS COMPRISING AT LEAST SIX CARBON ATOMS

FIELD

The present invention relates to processes for preparing isoprene and mono-olefins comprising at least six carbon atoms such as hexenes.

BACKGROUND

Isoprene is an important component for rubber manufacture, but global supply has been negatively impacted by a decline in the cracking of naphtha. Likewise 1-hexene could potentially be used as a co-monomer for polyethylene, but supply of 1-hexene is a limiting factor. The current invention describes a process to manufacture both isoprene and 1-hexene from inexpensive, readily available Raffinate II (mixed butenes). Since the demand and market price for these two important intermediates vary with time, the ability to shift or target the production to meet these demands from a common starting material would be commercially advantageous.

Among the known ways of manufacturing isoprene is through the dehydration of 2-methybutyraldehyde (2MBAL). For example, Journal of Catalysis (1999), 188(2), 291-299 describes the synthesis of isoprene via dehydration of 2-methylbutanal on boron and aluminum phosphate catalysts. Examples of suitable catalysts for the dehydration of 2-methylbutanal are given in U.S. Pat. Nos. 547,614, 4,587,372, 4,665,266, 4,734,538, EP 80449, EP 219042, GB 2227250, EP 272662, and Applied Catalysis (1986), 28(1-2), 161-8. The reaction is shown generally as:

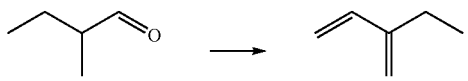

Mono-olefins having at least six carbon atoms are available from a number of sources. For example, such mono-olefins can be isolated as part of a refinery operation. There are also known synthesis techniques for making C6 or higher mono-olefins. For example, C8 mono-olefins can be made by the dimerization of butene.

Given their potential values in the marketplace, it would be desirable to have new ways of producing isoprene and mono-olefins comprising at least six carbon atoms.

SUMMARY

The present invention provides processes for preparing isoprene and mono-olefins comprising at least six carbon atoms. The present invention can advantageously take an inexpensive, readily available feed of mixed butenes (e.g., Raffinate II), and convert the mixed butenes to isoprene and/or hexene (or higher olefins). In some embodiments, processes of the present invention can advantageously be adjusted to adjust the relative amounts of isoprene and/or mono-olefins produced. This is particularly advantageous because the demand and market prices for these important intermediates (e.g., isoprene, 1-hexene, or other monoolefins) vary with time. The ability to shift or target the production rates to meet such demands is commercially advantageous.

In one aspect, a process for preparing isoprene and mono-olefins comprises at least six carbon atoms, the process comprising:
(a) hydroformylating a mixed C4 olefin stream, wherein the mixed C4 olefin stream comprises 1-butene, 2-butene, and optionally isobutene, with a hydroformylation catalyst, wherein the hydroformylation catalyst comprises rhodium with monodentate organophosphorous ligand and optionally polydentate organophosphorous ligand, to produce a mixture comprising linear and branched C5 aldehydes;
(b) separating the branched C5 aldehydes from the linear C5 aldehydes to provide a branched C5 aldehyde stream and a linear C5 aldehyde stream;
(c) dehydrating the branched C5 aldehydes in the branched C5 aldehyde stream using a dehydration catalyst to form a stream comprising isoprene;
(d) hydrogenating the linear C5 aldehydes in the linear C5 aldehyde stream to form a C5 alcohol stream;
(e) dehydrating the C5 alcohols in the C5 alcohol stream with a second dehydration catalyst to form a C5 olefin stream;
(f) hydroformylating the C5 olefins in the C5 olefin stream to generate a C6 aldehyde stream;
(g) hydrogenating the C6 aldehydes in the C6 aldehyde stream to form a C6 alcohol stream; and
(h) dehydrating the C6 alcohols in the C6 alcohol stream with a third dehydration catalyst to form a C6 olefin stream.

Processes of the present invention can be implemented in an integrated plant where the N:I ratio of the starting aldehydes can be varied to enable both isoprene and higher olefins to be produced to match market demand In some embodiments, and as discussed further herein, the process conditions that can be varied to adjust the ratio of n-valeraldehyde (used to prepare higher olefins) to 2-methybutyraldehyde (used to prepare isoprene) include changes in catalyst ligand ratios, changes in hydroformylation conditions (e.g., syngas partial pressures and olefin feed content), and, with multi-reactor designs, the partitioning of olefin, catalytic metal (typically rhodium), and/or conversion between the reactors. These parameters allow quick and reversible changes in the amount of feed available for the isoprene and higher olefin downstream production processes.

These and other embodiments are discussed in more detail in the Detailed Description below.

DETAILED DESCRIPTION

All references to the Periodic Table of the Elements and the various groups therein are to the version published in the CRC Handbook of Chemistry and Physics, 72nd Ed. (1991-1992) CRC Press, at page I-11.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent US version is so incorporated by reference) especially with respect to the disclosure of definitions (to the extent not inconsistent with any definitions specifically provided in this disclosure) and general knowledge in the art.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

As used herein, the term "ppmw" means parts per million by weight.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic (with or without heteroatoms) and cyclic, branched and unbranched, carbocyclic and heterocyclic, aromatic and nonaromatic organic compounds that can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxyalkyl, aminoalkyl, in which the number of carbons can range from 1 to 20 or more, preferably from 1 to 12, as well as hydroxy, halo, and amino The permissible substituents can be one or more and the same or different for appropriate organic compounds. This invention is not intended to be limited in any manner by the permissible substituents of organic compounds.

As used herein, the term "hydroformylation" is contemplated to include, but is not limited to, all hydroformylation processes that involve converting one or more substituted or unsubstituted olefinic compounds or a reaction mixture comprising one or more substituted or unsubstituted olefinic compounds to one or more substituted or unsubstituted aldehydes or a reaction mixture comprising one or more substituted or unsubstituted aldehydes. The aldehydes may be asymmetric or non-asymmetric.

The terms "hydroformylation reaction fluid," "hydroformylation reaction medium" and "hydroformylation catalyst solution" are used interchangeably herein, and may include, but are not limited to, a mixture comprising: (a) a metal-organophosphorous ligand complex catalyst, (b) free organophosphorous ligand, (c) aldehyde product formed in the reaction, (d) unreacted reactants, (e) a solvent for said metal-organophosphorous ligand complex catalyst and said free organophosphorous ligand, and, optionally, (f) one or more phosphorus acidic compounds, which may be dissolved and/or suspended, formed in the reaction. The reaction fluid can encompass, but is not limited to, (a) a fluid in a reaction zone, (b) a fluid stream on its way to a separation zone, (c) a fluid in a separation zone, (d) a recycle stream, (e) a fluid withdrawn from a reaction zone or separation zone, (f) a withdrawn fluid being treated with an acid removal system such as an extractor or other immiscible fluid contacting system, (g) a treated or untreated fluid returned to a reaction zone or separation zone, (h) a fluid in an external cooler, and (i) ligand decomposition products and components derived from them, such as oxides, sulfides, salts, oligomers, and the like.

As used herein, the terms "n-valeraldehyde", "NVal", "n-valeraldehyde stream", and "NVal stream" are used interchangeably to describe a stream comprising ≥97% linear valeraldehyde. The NVal stream is derived from the hydroformylation of butene or mixed butenes and may also comprise less than three percent branched aldehydes.

As used herein, the terms "2-methylbutyraldehyde", "2MBal", "2-methylbutraldehyde stream", and "2MBal stream" are used interchangeably to describe a stream comprising ≥97% 2-methylbutryaldehyde. The 2MBal stream is derived from the hydroformylation of butene or mixed butenes and may also comprise less than three percent NVal.

As used herein, the terms "pentanol", and "pentanol stream" are used interchangeably to describe a stream derived from NVal hydrogenation. The pentanol stream may also comprise less than four percent 2-methylbutanol.

As used herein, the terms "pentene" and "pentene stream" are used interchangeably to describe a stream comprising the product of pentanol dehydration.

As used herein, the terms "hexanal" and "hexanal stream" are used interchangeably to describe a stream comprising linear hexanal. The stream is derived from the hydroformylation of pentene and may further comprise branched C6 aldehyde.

As used herein, the terms "hexanol" and "hexanol stream" are used interchangeably to describe a stream comprising the product of hexanal hydrogenation and may comprise linear and branched hexanol.

As used herein, the terms "hexene" and "hexene stream" are used interchangeably to describe a stream comprising the product of hexanol dehydration and may comprise linear and branched hexene.

"Hydrolyzable organophosphorous ligands" are trivalent phosphorous ligands that contain at least one P—Z bond wherein Z is oxygen, nitrogen, chlorine, fluorine or bromine. Examples include, but are not limited to, phosphites, phosphino-phosphites, bisphosphites, phosphonites, bisphosphonites, phosphinites, phosphoramidites, phosphino-phosphoramidites, bisphosphoramidites, fluorophosphites, and the like. The ligands may include chelate structures and/or may contain multiple P—Z moieties such as polyphosphites, polyphosphoramidites, etc. and mixed P—Z moieties such as phosphite-phosphoramidites, flurophosphite-phosphites, and the like. The hydrolysable organophosphorous ligands may be monodentate ligands, bidentate ligands, or polydentate ligands. As used herein, the terms "monodentate ligand" refer to ligands with only one trivalent phosphorous atom per molecule, "bidentate ligand" refers to ligands with two trivalent phosphorous atoms per molecule, and "polydentate ligand" refers to ligands with two or more trivalent phosphorous atoms per molecule. For example, organobisphosphite ligands are bidentate ligands that contain two trivalent phosphorous atoms, each with three P—Z moieties (typically Z=O) whereas organomonophosphites are monodentate ligands with only one P—Z moiety.

The term "free ligand" means ligand that is not complexed with (tied to or bound to) the metal, e.g., metal atom, of the complex catalyst.

The present invention relates to processes for preparing isoprene and mono-olefins comprising at least six carbon atoms. In one aspect, the process comprises:
  (a) hydroformylating a mixed C4 olefin stream, wherein the mixed C4 olefin stream comprises 1-butene, 2-butene, and optionally isobutene, with a hydroformylation catalyst, wherein the hydroformylation catalyst comprises rhodium with monodentate organophosphorous ligand and optionally polydentate organophosphorous ligand, to produce a mixture comprising linear and branched C5 aldehydes;
  (b) separating the branched C5 aldehydes from the linear C5 aldehydes to provide a branched C5 aldehyde stream and a linear C5 aldehyde stream;

(c) dehydrating the branched C5 aldehydes in the branched C5 aldehyde stream using a dehydration catalyst to form a stream comprising isoprene;
(d) hydrogenating the linear C5 aldehydes in the linear C5 aldehyde stream to form a C5 alcohol stream;
(e) dehydrating the C5 alcohols in the C5 alcohol stream with a second dehydration catalyst to form a C5 olefin stream;
(f) hydroformylating the C5 olefins in the C5 olefin stream to generate a C6 aldehyde stream;
(g) hydrogenating the C6 aldehydes in the C6 aldehyde stream to form a C6 alcohol stream; and
(h) dehydrating the C6 alcohols in the C6 alcohol stream with a third dehydration catalyst to form a C6 olefin stream.

In some embodiments, the monodentate organophosphorous ligand is a monophosphite. In some embodiments, the monodentate organophosphorous ligand is a monophosphine. In some further embodiments, the hydroformylation catalyst further comprises polydentate organophosphorous ligand, the polydentate organophosphorous ligand is a bisphosphite, and the monodentate organophosphorous ligand is a monophosphite.

In some embodiments, the ratio of linear and branched C5 aldehydes produced in step (a) is adjusted to match a target ratio of isoprenes and C6 olefins in steps (c) and (h), respectively. In some embodiments, the hydroformylation catalyst comprises a polydentate organophosphorous ligand, and the ratio of polydentate organophosphorous ligand to rhodium is less than 1:1.4. In some embodiments, the hydroformylation in step (a) is conducted in one more reaction zones, and wherein the ratio of linear to branched C5 aldehydes in the mixture of step (a) is increased by increasing the ratio of polydentate organophosphorus ligand to rhodium in at least one reaction zone. In some embodiments, the hydroformylation in step (a) comprises contacting the mixed C4 olefin stream with synthesis gas and the hydroformylation catalyst at hydroformylation conditions including a synthesis gas partial pressure, and the ratio of linear to branched C5 aldehydes in the mixture of step (a) is increased by decreasing the synthesis gas partial pressure.

In some embodiments, the hydroformylation in step (a) comprises contacting the mixed C4 olefin stream with synthesis gas and the hydroformylation catalyst in first and subsequent reaction zones and at hydroformylation conditions that include a mixed C4 olefin partial pressure, and the ratio of linear to branched C5 aldehydes in the mixture of step (a) is increased by increasing the mixed C4 olefin partial pressure in the first reaction zone. In some further embodiments, the mixed C4 olefin partial pressure in the first reaction zone can be changed by one or more of the following: (1) increasing the temperature in the first reaction zone; (2) reducing the amount of mixed C4 olefin provided to a subsequent reaction zone; and/or (3) changing the olefin feed rate to the first reaction zone.

In some embodiments, the hydroformylation in step (a) is conducted in one or more reaction zones, and wherein the ratio of linear to branched C5 aldehydes in the mixture of step (a) is increased by increasing the transition metal concentration in at least one reaction zone. In some further embodiments, the transition metal concentration in a first reaction zone may be changed by one or more of the following: (1) partitioning catalyst recycle from a product separation zone between a first reaction zone and one or more subsequent reaction zones; or (2) adding transition metal without any ligand either as a transition metal precursor or a metal-organomonodentate compound; or (3) decreasing the transition metal concentration in the first reaction zone by removing up to 20% of the transition metal catalyst from the reaction system into a separate vessel; or (4) returning transition metal catalyst previously removed (as in option (3)) to the first reaction zone.

In some embodiments, the C5 olefin stream further comprises C5 alcohols and ethers, and the process further comprises separating the C5 alcohols and ethers from the C5 olefin stream and returning the separated C5 alcohols and ethers to dehydration step (e).

In some embodiments, the hydroformylation in step (f) is conducted in the same reactor or plurality of reactors as the hydroformylation in step (a).

In some embodiments, the target ratio of isoprene from step (c) relative to C6 olefin produced from step (h) is from 2:1 to 1:50. In some embodiments, the target ratio of isoprene from step (c) relative to C6 olefin produced from step (h) is from 1.5:1 to 1:1.5. In some embodiments, the target ratio of isoprene from step (c) relative to C6 olefin produced from step (h) is from 1:1.1 to 1:20. In some embodiments, the target ratio of isoprene from step (c) relative to C6 olefin produced from step (h) is from 1:1 to 1:30. In some embodiments, the target ratio of isoprene from step (c) relative to C6 olefin produced from step (h) is from 1:5 to 1:25.

In some embodiments, the C5 olefin stream comprises linear C5 alpha olefins, linear C5 internal olefins, and branched C5 olefins.

In some embodiments, the process further comprises adjusting the composition of the mixed C4 olefin stream prior to step (a). For example, if it was desired to produce more isoprene, the composition of the mixed C4 olefin stream could be adjusted to increase the 2-butene content using techniques known to those of ordinary skill in the art based on the teachings herein.

In some embodiments, mono-olefins having seven, eight, or higher carbons can be produced by the inclusion of additional process steps. For example, to make mono-olefins having seven carbons, processes of the present invention can further comprise (i) hydroformylating the C6 olefins in the C6 olefin stream to generate a C7 aldehyde stream; (j) hydrogenating the C7 aldehydes in the C7 aldehyde stream to form a C7 alcohol stream; and (k) dehydrating the C7 alcohols in the C7 alcohol stream with a fourth dehydration catalyst to form a C7 olefin stream. The C7 olefin stream can also be used to make C8 olefins in some further embodiments of the present invention. For example, such processes can further comprise (l) hydroformylating the C7 olefins in the C7 olefin stream to generate a C8 aldehyde stream; (m) hydrogenating the C8 aldehydes in the C8 aldehyde stream to form a C8 alcohol stream; and (n) dehydrating the C8 alcohols in the C8 alcohol stream with a fifth dehydration catalyst to form a C8 olefin stream.

Hydrogen and carbon monoxide are required for the process and in particular, hydroformylation reactions in the process. These may be obtained from any suitable source, including petroleum cracking and refinery operations. Syngas mixtures are preferred as a source of hydrogen and CO.

Syngas (from synthesis gas) is the name given to a gas mixture that contains varying amounts of CO and $H_2$. Production methods are well known and include, for example: (1) steam reforming and partial oxidation of natural gas or liquid hydrocarbons, and (2) the gasification of coal and/or biomass. Hydrogen and CO typically are the main components of syngas, but syngas may contain carbon dioxide and inert gases such as $CH_4$, $N_2$ and Ar. The molar ratio of $H_2$ to CO varies greatly but generally ranges from 1:100 to 100:1 and preferably between 1:10 and 10:1. Syngas is commercially available and is often used as a fuel source or as an intermediate for the production of other chemicals. The most preferred $H_2$:CO molar ratio for chemical production is between 3:1 and 1:3 and usually is targeted to be between about 1:2 and 2:1 for most hydroformylation applications.

Hydroformylation Steps

The olefin starting material reactants that may be employed in the first hydroformylation reaction according to processes of the present invention include olefinic unsaturated compounds containing 4 carbon atoms. Illustrative mixtures of olefinic starting materials that can be employed in the first hydroformylation reaction include, for example, mixed butenes, e.g., Raffinate I and II.

The subject invention is especially useful for the production of non-optically active C5 or higher aldehydes, by hydroformylating achiral alpha-olefins containing from 4 carbon atoms in an initial step. Illustrative alpha and internal olefins include, for example, 1-butene, cis and trans 2-butene, and isobutene. One or more of such butenes can be provided as part of a mixed C4 olefin stream to an initial hydroformylation process. In some embodiments, the mixed C4 olefin stream advantageously includes a blend of 1-butene and 2-butene to provide downstream flexibility in the production of isoprene and mono-olefins.

A solvent advantageously is employed in the hydroformylation processes. Any suitable solvent that does not unduly interfere with the hydroformylation process can be used. By way of illustration, suitable solvents for rhodium catalyzed hydroformylation include those disclosed, for example, in U.S. Pat. Nos. 3,527,809; 4,148,830; 5,312,996; and 5,929,289. Non-limiting examples of suitable solvents include saturated hydrocarbons (alkanes), aromatic hydrocarbons, water, ethers, polyethers, alkylated polyethers, aldehydes, ketones, nitriles, alcohols, esters, and aldehyde condensation products. Specific examples of solvents that can be used include: tetraglyme, pentanes, cyclohexane, heptanes, benzene, xylene, toluene, diethyl ether, tetrahydrofuran, butyraldehyde, and benzonitrile. The organic solvent may also contain dissolved water up to the saturation limit. In general, with regard to the production of achiral (non-optically active) aldehydes, it is preferred to employ aldehyde compounds corresponding to the aldehyde products desired to be produced and/or higher boiling aldehyde liquid condensation by-products as the main organic solvents as is common in the art. Such aldehyde condensation by-products can also be preformed if desired and used accordingly. Illustrative preferred solvents employable in the production of aldehydes include ketones (e.g. acetone and methylethyl ketone), esters (e.g. ethyl acetate, di-2-ethylhexyl phthalate, 2,2,4-trimethyl-1,3-pentanediol monoisobutyrate), hydrocarbons (e.g. toluene), nitrohydrocarbons (e.g. nitrobenzene), ethers (e.g. tetrahydrofuran (THF)) and sulfolane. In rhodium catalyzed hydroformylation, it may be preferred to employ, as a primary solvent, aldehyde compounds corresponding to the aldehyde products desired to be produced and/or higher boiling aldehyde liquid condensation by-products, for example, as might be produced in situ during the hydroformylation process, as described for example in U.S. Pat. Nos. 4,148,830 and 4,247,486. Indeed, while one may employ, if desired, any suitable solvent at the start-up of a continuous process, the primary solvent will normally eventually comprise both aldehyde products and higher boiling aldehyde liquid condensation by-products ("heavies"), due to the nature of the continuous process. The amount of solvent is not especially critical and need only be sufficient to provide the reaction medium with the desired amount of transition metal concentration. Typically, the amount of solvent ranges from about 5 percent to about 95 percent by weight, based on the total weight of the reaction fluid. Mixtures of two or more solvents may also be employed.

The catalyst useful in the hydroformylation steps in processes of the present invention comprise a catalytic metal. The catalytic metal can include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with preferred metals being rhodium, cobalt, iridium and ruthenium, more preferably rhodium, cobalt and ruthenium, especially rhodium. The hydroformylation steps may employ the same or different catalytic metals.

The number of available coordination sites on such metals is well known in the art. Thus the catalytic species, which may comprise a complex catalyst mixture, may comprise monomeric, dimeric or higher nuclearity forms, which are preferably characterized by at least one organophosphite-containing molecule complexed per one molecule of metal, e.g., rhodium. For instance, it is considered that the catalytic species of the preferred catalyst employed in a hydroformylation reaction may be complexed with carbon monoxide and hydrogen in addition to the organophosphite ligands in view of the carbon monoxide and hydrogen gas employed by the hydroformylation reaction.

Illustrative metal-organophosphorous ligand complexes employable in such hydroformylation reactions encompassed by this invention include metal-organophosphorous ligand complex catalysts. The catalysts, as well as methods for their preparation, are well known in the art and include those disclosed in the above-mentioned patents. In general, such catalysts may be preformed or formed in situ as described in such references and consist essentially of metal in complex combination with an organophosphorous ligand. It is believed that carbon monoxide is also present and complexed with the metal in the active species. The active species may also contain hydrogen directly bonded to the metal.

The permissible organophosphorous ligands that make up the metal-organophosphorous ligand complexes and free organophosphorous ligand include monodentate organophosphorous ligands, bidentate organophosphorous ligands, and/or polydentate organophosphorous ligands including, for example, mono-, di-, tri- and higher polyorganophosphites. Mixtures of such ligands may be employed if desired in the metal-organophosphorous ligand complex catalyst and/or free ligand and such mixtures may be the same or different. This invention is not intended to be limited in any manner by the permissible organophosphorous ligands or mixtures thereof. It is to be noted that the successful practice of this invention does not depend and is not predicated on the exact structure of the metal-organophosphorous ligand complex species, which may be present in their mononuclear, dinuclear and/or higher nuclearity forms. Indeed, the exact structure is not known. While not intending to be bound to any theory or mechanistic discourse, it appears that the catalytic species may in its simplest form consist essentially of the metal in complex combination with the organophosphorous ligand and carbon monoxide and/or hydrogen.

The term "complex" as used herein means a coordination compound formed by the union of one or more electronically rich molecules or atoms capable of independent existence with one or more electronically poor molecules or atoms, each of which is also capable of independent existence. For example, the organophosphorous ligands employable herein may possess one or more phosphorus donor atoms, each having one available or unshared pair of electrons that are each capable of forming a coordinate bond independently or possibly in concert (e.g., via chelation) with the metal. Carbon monoxide, which is also properly classified as a ligand, can also be present and coordinated to the metal. The ultimate composition of the complex catalyst may also contain an additional ligand, e.g., hydrogen or an anion satisfying the coordination sites or nuclear charge of the metal. Illustrative additional ligands include, for example, halogen (Cl, Br, I), alkyl, aryl, substituted aryl, acyl, $CF_3$, $C_2F_5$, CN, $(R)_2PO$ and $RP(O)(OH)O$ (wherein each R is the same or different and is a substituted or unsubstituted hydrocarbon radical, e.g., the alkyl or aryl), acetate, acetylacetonate, $SO_4$, $PF_4$, $PF_6$, $NO_2$, $NO_3$, $CH_3$, $CH_2=CHCH_2$, $CH_3CH=CHCH_2$, $C_6H_5CN$, $CH_3CN$, $NH_3$, pyridine, $(C_2H_5)_3N$, mono-olefins, diolefins and triolefins, tetrahydrofuran, and the like. The complex species are preferably free of any additional organic ligand or anion that might poison the catalyst or have an undue adverse effect on catalyst performance. It is preferred in the metal-organophosphite ligand complex catalyzed hydroformylation reactions that the active catalysts be free of halogen and sulfur directly bonded to the metal, although such may not be absolutely necessary. The hydroformylation steps used in processes of the present invention may employ the same or different catalytic metal complexes. The organophosphorous compounds that may serve as the ligand of the metal-organophosphorous ligand complex catalyst and/or free ligand may be of the achiral (optically inactive) or chiral (optically active) type and are well known in the art. Achiral organophosphorous ligands are preferred.

Among the organophosphorous ligands that may serve as the ligand of the metal-organophosphorous ligand complex catalyst are monoorganophosphite, diorganophosphite, triorganophosphite and organopolyphosphite compounds. Such organophosphorous ligands and/or methods for their preparation are well known in the art.

Representative monoorganophosphites may include those having the formula:

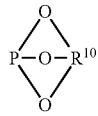      <<I>> wherein $R^{10}$ represents a substituted or unsubstituted trivalent hydrocarbon radical containing from 4 to 40 carbon atoms or greater, such as trivalent acyclic and trivalent cyclic radicals, e.g., trivalent alkylene radicals such as those derived from 1,2,2-trimethylolpropane and the like, or trivalent cycloalkylene radicals such as those derived from 1,3,5-trihydroxycyclohexane, and the like. Such monoorganophosphites may be found described in greater detail, for example, in U.S. Pat. No. 4,567,306.

Representative diorganophosphites may include those having the formula:

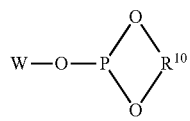      <<II>> wherein $R^{20}$ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater.

Representative substituted and unsubstituted monovalent hydrocarbon radicals represented by W in the above Formula (II) include alkyl and aryl radicals, while representative substituted and unsubstituted divalent hydrocarbon radicals represented by $R^{20}$ include divalent acyclic radicals and divalent aromatic radicals. Illustrative divalent acyclic radicals include, for example, alkylene, alkylene-oxy-alkylene, alkylene-S-alkylene, cycloalkylene radicals, and, alkylene-$NR^{24}$-alkylene wherein $R^{24}$ is hydrogen or a substituted or unsubstituted monovalent hydrocarbon radical, e.g., an alkyl radical having 1 to 4 carbon atoms. The more preferred divalent acyclic radicals are the divalent alkylene radicals such as disclosed more fully, for example, in U.S. Pat. Nos. 3,415,906 and 4,567,302 and the like. Illustrative divalent aromatic radicals include, for example, arylene, bisarylene, arylene-alkylene, arylene-alkylene-arylene, arylene-oxy-arylene, arylene-$NR^{24}$-arylene wherein $R^{24}$ is as defined above, arylene-S-arylene, and arylene-S-alkylene, and the like. More preferably $R^{20}$ is a divalent aromatic radical such as disclosed more fully, for example, in U.S. Pat. Nos. 4,599,206, 4,717,775, 4,835,299, and the like.

Representative of a more preferred class of diorganophosphites are those of the formula:

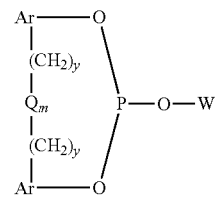      <<III>> wherein W is as defined above, each Ar is the same or different and represents a substituted or unsubstituted aryl radical, each y is the same or different and is a value of 0 or 1, Q represents a divalent bridging group selected from $-C(R^{33})_2-$, $-O-$, $-S-$, $-NR^{24}-$, $Si(R^{35})_2$ and $-CO-$, wherein each $R^{33}$ is the same or different and represents hydrogen, an alkyl radical having from 1 to 12 carbon atoms, phenyl, tolyl, and anisyl, $R^{24}$ is as defined above, each $R^{35}$ is the same or different and represents hydrogen or a methyl radical, and m has a value of 0 or 1. Such diorganophosphites are described in greater detail, for example, in U.S. Pat. Nos. 4,599,206, 4,717,775, and 4,835,299.

Representative triorganophosphites may include those having the formula:

      <<IV>> wherein each $R^{46}$ is the same or different and is a substituted or unsubstituted monovalent hydrocarbon radical e.g., an alkyl, cycloalkyl, aryl, alkaryl and aralkyl radicals that may contain from 1 to 24 carbon atoms. Illustrative triorganophosphites include, for example, trialkyl phosphites, dialkylaryl phosphites, alkyldiaryl phosphites, triaryl phosphites, and the like, such as, for example, trimethyl phosphite, triethyl phosphite, butyldiethyl phosphite, tri-n-propyl phosphite, tri-n-butyl phosphite, tri-2-ethylhexyl phosphite, tri-n-octyl phosphite, tri-n-dodecyl phosphite, dimethylphenyl phosphite, diethylphenyl phosphite, methyldiphenyl phosphite, ethyldiphenyl phosphite, triphenyl phosphite, trinaphthyl phosphite, bis(3,6,8-tri-t-butyl-2-naphthyl)methylphosphite, bis(3,6,8-tri-t-butyl-2-naphthyl)cyclohexylphosphite, tris(3,6-di-t-butyl-2-naphthyl)phosphite, bis(3,6,8-tri-t-butyl-2-naphthyl)(4-biphenyl)phosphite, bis(3,6,8-tri-t-butyl-2-naphthyl)phenylphosphite, bis(3,6,8-tri-t-butyl-2-naphthyl)(4-benzoylphenyl)phosphite, bis(3,6,8-tri-t-butyl-2-naphthyl)(4-sulfonylphenyl)phosphite, and the like. The most preferred triorganophosphite is tris(2,4-di-t-butylphenyl)phosphite. Such triorganophosphites are described in greater detail, for example, in U.S. Pat. Nos. 3,527,809 and 4,717,775.

Other hydrolysable monodentate organophosphorous ligands may also be employed such as organophosphonites, phosphoramidites, fluorophosphonites.

Representative organopolyphosphites contain two or more tertiary (trivalent) phosphorus atoms and may include those having the formula:

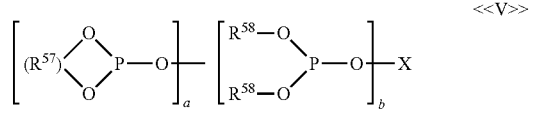

wherein X represents a substituted or unsubstituted n-valent organic bridging radical containing from 2 to 40 carbon atoms, each $R^{57}$ is the same or different and represents a divalent organic radical containing from 4 to 40 carbon atoms, each $R^{58}$ is the same or different and represents a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b. When "a" has a value of 2 or more, each $R^{57}$ radical may be the same or different. Each $R^{58}$ radical may also be the same or different in any given compound.

Representative n-valent (preferably divalent) organic bridging radicals represented by X and representative divalent organic radicals represented by $R^{57}$ above, include both acyclic radicals and aromatic radicals, such as alkylene, alkylene-$Q_m$-alkylene, cycloalkylene, arylene, bisarylene, arylene-alkylene, and arylene-$(CH_2)_y$-$Q_m$-$(CH_2)_y$-arylene radicals, and the like, wherein each Q, y and m are as defined above in Formula (III). The more preferred acyclic radicals represented by X and $R^{57}$ above are divalent alkylene radicals, while the more preferred aromatic radicals represented by X and $R^{57}$ above are divalent arylene and bisarylene radicals, such as disclosed more fully, for example, in U.S. Pat. Nos. 4,769,498; 4,774,361: 4,885,401; 5,179,055; 5,113,022; 5,202,297; 5,235,113; 5,264,616; 5,364,950 and 5,527,950. Representative preferred monovalent hydrocarbon radicals represented by each $R^{58}$ radical above include alkyl and aromatic radicals.

Illustrative preferred organopolyphosphites may include bisphosphites such as those of Formulas (VI) to (VIII) below:

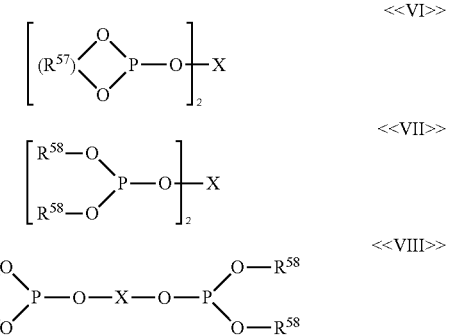

wherein each $R^{57}$, $R^{58}$ and X of Formulas (VI) to (VIII) are the same as defined above for Formula (V). Preferably each $R^{57}$ and X represents a divalent hydrocarbon radical selected from alkylene, arylene, arylene-alkylene-arylene, and bisarylene, while each $R^{58}$ radical represents a monovalent hydrocarbon radical selected from alkyl and aryl radicals. Organophosphite ligands of such Formulas (V) to (VIII) may be found disclosed, for example, in U.S. Pat. Nos. 4,668,651; 4,748,261; 4,769,498; 4,774,361; 4,885,401; 5,113,022; 5,179,055; 5,202,297; 5,235,113; 5,254,741; 5,264,616; 5,312,996; 5,364,950; and 5,391,801.

$R^{10}$, $R^{20}$, $R^{46}$, $R^{57}$, $R^{58}$, Ar, Q, X, m, and y in Formulas (VI) to (VIII) are as defined above. Most preferably X represents a divalent aryl-$(CH_2)_y$-$(Q)_m$-$(CH_2)_y$-aryl radical wherein each y individually has a value of 0 or 1; m has a value of 0 or 1 and Q is —O—, —S— or —$C(R^{35})_2$— where each $R^{35}$ is the same or different and represents hydrogen or a methyl radical. More preferably each alkyl radical of the above defined $R^8$ groups may contain from 1 to 24 carbon atoms and each aryl radical of the above-defined Ar, X, $R^{57}$ and $R^{58}$ groups of the above Formulas (VI) to (VII) may contain from 6 to 18 carbon atoms and said radicals may be the same or different, while the preferred alkylene radicals of X may contain from 2 to 18 carbon atoms and the preferred alkylene radicals of $R^{57}$ may contain from 5 to 18 carbon atoms. In addition, preferably the divalent Ar radicals and divalent aryl radicals of X of the above formulas are phenylene radicals in which the bridging group represented by —$(CH_2)_y$-$(Q)_m$-$(CH_2)_y$— is bonded to said phenylene radicals in positions that are ortho to the oxygen atoms of the formulas that connect the phenylene radicals to their phosphorus atom of the formulae. It is also preferred that any substituent radical when present on such phenylene radicals be bonded in the para and/or ortho position of the phenylene radicals in relation to the oxygen atom that bonds the given substituted phenylene radical to its phosphorus atom.

Any of the $R^{10}$, $R^{20}$, $R^{57}$, $R^{58}$, W, X, Q and Ar radicals of such organophosphites of Formulas (I) to (VIII) above may be substituted if desired, with any suitable substituent containing from 1 to 30 carbon atoms that does not unduly adversely affect the desired result of the process of this invention. Substituents that may be on said radicals in addition to corresponding hydrocarbon radicals such as alkyl, aryl, aralkyl, alkaryl and cyclohexyl substituents, may include for example silyl radicals such as —$Si(R^{35})_3$; amino radicals such as —$N(R^{15})_2$; phosphine radicals such as -aryl-P(R$^{15}$)$_2$; acyl radicals such as —C(O)R$^{15}$ acyloxy radicals such as —OC(O)R$^{15}$; amido radicals such as —CON(R$^{15}$)$_2$ and —N(R$^{15}$)COR$^{15}$; sulfonyl radicals such as —SO$_2$ R$^{15}$, alkoxy radicals such as —OR$^{15}$; sulfinyl radicals such as —SOR$^{15}$, phosphonyl radicals such as —P(O)(R$^{15}$)$_2$, as well as halo, nitro, cyano, trifluoromethyl, hydroxy radicals, and the like, wherein each R$^{15}$ radical individually represents the same or different monovalent hydrocarbon radical having from 1 to 18 carbon atoms (e.g., alkyl, aryl, aralkyl, alkaryl and cyclohexyl radicals), with the proviso that in amino substituents such as —N(R$^{15}$)$_2$ each R$^{15}$ taken together can also represent a divalent bridging group that forms a heterocyclic radical with the nitrogen atom, and in amido substituents such as —C(O)N(R$^{15}$)$_2$ and —N(R$^{15}$)COR$^{15}$ each R$^{15}$ bonded to N can also be hydrogen. Any of the substituted or unsubstituted hydrocarbon radicals groups that make up a particular given organophosphite may be the same or different.

More specifically illustrative substituents include primary, secondary and tertiary alkyl radicals such as methyl, ethyl, n-propyl, isopropyl, butyl, sec-butyl, t-butyl, neopentyl, n-hexyl, amyl, sec-amyl, t-amyl, iso-octyl, decyl, octadecyl, and the like; aryl radicals such as phenyl, naphthyl and the like; aralkyl radicals such as benzyl, phenylethyl, triphenylmethyl, and the like; alkaryl radicals such as tolyl, xylyl, and the like; alicyclic radicals such as cyclopentyl, cyclohexyl, 1-methylcyclohexyl, cyclooctyl, cyclohexylethyl, and the like; alkoxy radicals such as methoxy, ethoxy, propoxy, t-butoxy, —OCH$_2$CH$_2$OCH$_3$, —O(CH$_2$CH$_2$)$_2$OCH$_3$, —O(CH$_2$CH$_2$)$_3$OCH$_3$, and the like; aryloxy radicals such as phenoxy and the like; as well as silyl radicals such as —Si(CH$_3$)$_3$, —Si(OCH$_3$)$_3$, —Si(C$_3$H$_7$)$_3$, and the like; amino radicals such as —NH$_2$, —N(CH$_3$)$_2$, —NHCH$_3$, —NH(C$_2$H$_5$), and the like; arylphosphine radicals such as —P(C$_6$H$_5$)$_2$, and the like; acyl radicals such as —C(O)CH$_3$, —C(O)C$_2$H$_5$, —C(O)C$_6$H$_5$, and the like; carbonyloxy radicals such as —C(O)OCH$_3$ and the like; oxycarbonyl radicals such as —O(CO)C$_6$H$_5$, and the like; amido radicals such as —CONH$_2$, —CON(CH$_3$)$_2$, —NHC(O)CH$_3$, and the like; sulfonyl radicals such as —S(O)$_2$C$_2$H$_5$ and the like; sulfinyl radicals such as —S(O)CH$_3$ and the like; sulfidyl radicals such as —SCH$_3$, —SC$_2$H$_5$, —SC$_6$H$_5$, and the like; phosphonyl radicals such as —P(O)(C$_6$H$_5$)$_2$, —P(O)(CH$_3$)$_2$, —P(O)(C$_2$H$_5$)$_2$, —P(O)(C$_3$H$_7$)$_2$, —P(O)(C$_4$H$_9$)$_2$, —P(O)(C$_6$H$_{13}$)$_2$, —P(O)CH$_3$(C$_6$H$_5$), —P(O)(H)(C$_6$H$_5$), and the like.

Specific illustrative examples of such organophosphite ligands include the following:

2-t-butyl-4-methoxyphenyl(3,3'-di-t-butyl-5,5'-dimethoxy-1,1'-biphenyl-2,2'-diyl)phosphite, methyl(3,3'-di-t-butyl-5,5'-dimethoxy-1,1'-biphenyl-2,2'-diyl)phosphite, 6,6'-[[4,4'-bis(1,1-dimethylethyl)-[1,1'-binaphthyl]-2,2'-diyl]bis(oxy)]bis-dibenzo[d,f][1,3,2]-dioxaphosphepin, 6,6'-[[3,3'-bis(1,1-dimethylethyl)-5,5'-dimethoxy-[1,1'-biphenyl]-2,2'-diyl]bis(oxy)]bis-dibenzo[d,f][1,3,2]dioxaphosphepin, 6,6'-[[3,3',5,5'-tetrakis(1,1-dimethylpropyl)-[1,1'-biphenyl]-2,2'-diyl]bis(oxy)]bis-dibenzo[d,f][1,3,2] dioxaphosphepin, 6,6'-[[3,3',5,5'-tetrakis(1,1-dimethylethyl)-1,1'-biphenyl]-2,2'-diyl]bis(oxy)]bis-dibenzo[d,f][1,3,2]-dioxaphosphepin, (2R,4R)-di [2,2'-(3,3',5,5'-tetrakis-tert-amyl-1,1'-biphenyl)]-2,4-pentyldiphosphite, (2R,4R)-di[2,2'-(3,3',5,5'-tetrakis-tert-butyl-1,1'-biphenyl)]-2,4-pentyldiphosphite, (2R,4R)-di[2, 2'-(3,3'-di-amyl-5,5'-dimethoxy-1,1'-biphenyl)]2,4-pentyldiphosphite, (2R,4R)-di[2,2'-(3,3'-di-tert-butyl-5,5'-dimethyl-1,1'-biphenyl)]-2,4-pentyldiphosphite, (2R,4R)-di [2,2'-(3,3'-di-tert-butyl-5,5'-diethoxy-1,1'-biphenyl)]-2,4-pentyldiphosphite, (2R,4R),di[2,2'(3,3'di-tert,butyl-5,5-diethyl-1,1-biphenyl)]-2,4-pentyldiphosphite, (2R, 4R)di[2, 2'-(3,3'-di-tert-butyl-5,5'-dimethoxy-1,1'-biphenyl)]-2,4-pentyldiphosphite, 6-[[2'-[(4,6-bis(1,1-dimethylethyl)-1,3,2-benzodioxaphosphol-2-yl)oxy]-3,3'-bis(1,1-dimethylethyl)-5,5'-dimethoxy[1,1'-biphenyl]-2-yl]oxy ]-4,8-bis(1,1-dimethylethyl)-2,10-dimethoxydibenzo [d,f] [1,3,2] dioxaphosphepin, 6-[[2'-[1,3,2-benzodioxaphosphol-2-yl]oxy]-3,3'-bis(1,1-dimethylethyl)-5,5'-dimethoxy[1,1'-biphenyl]-2-yl]oxy]-4,8-bis(1,1-dimethylethyl)-2,10-dimethoxydibenzo[d,f] [1,3,2]dioxaphosphepin, 6-[[2'-[(5, 5-dimethyl-1,3,2-dioxaphosphorinan-2-yl) oxy]-3,3'-bis(1, 1-dimethylethyl)-5,5'-dimethoxy[1,1'-biphenyl]-2-yl]oxy]-4,8-bis(1,1-dimethylethyl)-2,10-dimethoxydibenzo[d,f] [1,3,2]dioxaphosphepin, 2'-[[4,8-bis(1,1-dimethylethyl)-2,10-dimethoxydibenzo[d,f][1,3,2]-dioxaphosphepin-6-yl] oxy]-3,3'-bis (1,1-dimethylethyl)-5,5'-dimethoxy[1,1'-biphenyl]-2-yl bis(4-hexylphenyl)ester of phosphorous acid, 2-[[2-[[4,8,-bis(1,1-dimethylethyl), 2,10-dimethoxydibenzo-[d,f] [1,3,2]dioxophosphepin-6-yl]oxy]-3-(1, 1-dimethylethyl)-5-methoxyphenyl]methyl]-4-methoxy, 6-(1,1-dimethylethyl)phenyl, diphenyl ester of phosphorous acid, 3-methoxy-1,3-cyclohexamethylene tetrakis[3,6-bis(1, 1-dimethylethyl)-naphthalenyl]ester of phosphorous acid, 2,5-bis(1,1-dimethylethyl)-1,4-phenylene tetrakis[2,4-bis(1, 1-dimethylethyl)phenyl]ester of phosphorous acid, methylenedi-2,1-phenylene tetrakis[2,4-bis(1,1-dimethylethyl)phenyl]ester of phosphorous acid, and [1,1'-biphenyl]-2,2'-diyl tetrakis[2-(1,1-dimethylethyl)-4-methoxyphenyl]ester of phosphorous acid.

Other polyphosphites include calixarene-based bisphosphites such as disclosed in U.S. Pat. Nos. 7,906,688 and 8,741,173 and polyphosphoramidites such as disclosed in U.S. Pat. No. 7,615,645.

Triarylphosphines can also be employed in the process of this disclosure which comprises any organic compound comprising one phosphorus atom covalently bonded to three aryl or arylalkyl radicals, or combinations thereof. A mixture of triarylphosphine ligands may also be employed. Representative organomonophosphines include those having the formula:

<<IX>> wherein each R$^{29}$, R$^{30}$ and R$^{31}$ may be the same or different and represent a substituted or unsubstituted aryl radical containing from 6 to 40 carbon atoms or greater. Such triarylphosphines may be found described in greater detail, for example, in U.S. Pat. No. 3,527,809, the disclosure of which is incorporated herein by reference. Illustrative triarylphosphine ligands are triphenylphosphine, trinaphthylphine, tritolylphosphine, tri(p-biphenyl)phosphine, tri(p-methoxyphenyl) phosphine, tri(m-chlorophenyl)-phosphine, p-N,N-dimethylaminophenyl bis-phenyl phosphine, and the like. Triphenyl phosphine, i.e. the compound of Formula II wherein each R$^{29}$, R$^{30}$ and R$^{31}$ is phenyl, is an example of a preferred organomonophosphine ligand. Triarylphosphines would be most applicable to the second hydroformylation process.

As noted above, the metal-organophosphorous ligand complex catalysts may be formed by methods known in the art. The metal-organophosphorous ligand complex catalysts may be in homogeneous or heterogeneous form. For instance, preformed rhodium hydrido-carbonyl-organophosphorous ligand catalysts may be prepared and introduced into the reaction mixture of a hydroformylation process. More preferably, the rhodium-organophosphorous ligand complex catalysts can be derived from a rhodium catalyst precursor that may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$, and the like may be introduced into the reaction mixture along with the organophosphorous ligand for the in situ formation of the active catalyst. Preferably, rhodium dicarbonyl acetylacetonate is employed as a rhodium precursor and reacted in the presence of a solvent with the organophosphorous ligand to form a catalytic rhodium-organophosphorous ligand complex precursor that is introduced into the reactor along with excess (free) organophosphorous ligand for the in situ formation of the active catalyst. In any event, it is sufficient for the purposes of this invention that carbon monoxide, hydrogen and organophosphorous ligand compound are all ligands that are capable of being complexed with the metal and that an active metal-organophosphorous ligand complex catalyst is present in the reaction mixture under the conditions used in the hydroformylation reaction. Carbonyl and organophosphorous ligands, if not already complexed with the initial rhodium, may be complexed to the rhodium either prior to or in situ during the hydroformylation process.

By way of illustration, one potential catalyst precursor composition for hydroformylation reactions consists essentially of a solubilized rhodium carbonyl organophosphite ligand complex precursor, a solvent and, optionally, free organophosphite ligand. The preferred catalyst precursor composition can be prepared by forming a solution of rhodium dicarbonyl acetylacetonate, an organic solvent and a organophosphite ligand. The organophosphite ligand readily replaces one of the carbonyl ligands of the rhodium acetylacetonate complex precursor at room temperature as witnessed by the evolution of carbon monoxide gas. This substitution reaction may be facilitated by heating the solution if desired. Any suitable organic solvent in which both the rhodium dicarbonyl acetylacetonate complex precursor and rhodium organophosphite ligand complex precursor are soluble can be employed. The amounts of rhodium complex catalyst precursor, organic solvent and organophosphite ligand, as well as their preferred embodiments present in such catalyst precursor compositions may obviously correspond to those amounts employable in the hydroformylation process of this invention. Experience has shown that the acetylacetonate ligand of the precursor catalyst is replaced after the hydroformylation process has begun with a different ligand, e.g., hydrogen, carbon monoxide or organophosphite ligand, to form the active complex catalyst as explained above. The acetylacetone that is freed from the precursor catalyst under hydroformylation conditions is removed from the reaction medium with the product aldehyde and thus is in no way detrimental to the hydroformylation process. The use of such preferred rhodium complex catalytic precursor compositions provides a simple economical and efficient method for handling the rhodium precursor and hydroformylation start-up.

Accordingly, the metal-organophosphite ligand complex catalyst used for hydroformylation in some embodiments of processes of the present invention consists essentially of the metal complexed with carbon monoxide and a organophosphite ligand, said ligand being bonded (complexed) to the metal in a chelated and/or non-chelated fashion. Moreover, the terminology "consists essentially of", as used herein, does not exclude, but rather includes, hydrogen complexed with the metal, in addition to carbon monoxide and the organophosphite ligand. Further, such terminology does not exclude the possibility of other organic ligands and/or anions that might also be complexed with the metal. Materials in amounts that unduly adversely poison or unduly deactivate the catalyst are not desirable and so the catalyst most desirably is free of contaminants such as metal-bound halogen (e.g., chlorine, and the like) although such may not be absolutely necessary. The hydrogen and/or carbonyl ligands of an active metal-organophosphite ligand complex catalyst may be present as a result of being ligands bound to a precursor catalyst and/or as a result of in situ formation, e.g., due to the hydrogen and carbon monoxide gases employed in hydroformylation process.

As noted, the hydroformylation steps involved in some embodiments of processes of the present invention involve the use of a metal-organophosphorous ligand complex catalyst as described herein. Mixtures of such catalysts can also be employed if desired. The amount of metal-organophosphorous ligand complex catalyst present in the reaction fluid of a given hydroformylation process need only be that minimum amount necessary to provide the given metal concentration desired to be employed and that will furnish the basis for at least the catalytic amount of metal necessary to catalyze the particular hydroformylation process involved such as disclosed, for example, in the above-mentioned patents. In general, catalytic metal, e.g., rhodium, concentrations in the range of from 10 ppmw to 1000 ppmw, calculated as free metal in the reaction medium, should be sufficient for most processes, while it is generally preferred to employ from 10 to 500 ppmw of metal, and more preferably from 25 to 350 ppmw of metal. Analytical techniques for measuring catalytic metal concentrations are well known to the skilled person, and include atomic absorption (AA), inductively coupled plasma (ICP) and X-ray fluorescence (XRF); AA is typically preferred.

In addition to the metal-organophosphorous ligand complex catalyst, free organophosphorous ligand (i.e., ligand that is not complexed with the metal) may also be present in the reaction medium. The free organophosphorous ligand may correspond to any of the above-defined organophosphorous ligands discussed above as employable herein. It is preferred that the free organophosphorous ligand be the same as the organophosphorous ligand of the metal-organophosphorous ligand complex catalyst employed. However, such ligands need not be the same in any given process. The hydroformylation steps may involve from 0.1 moles or less to 100 moles or higher of free organophosphorous ligand per mole of metal in the reaction medium. Preferably, the hydroformylation steps are carried out in the presence of from 1 to 50 moles of free organophosphorous ligand per mole of metal present in the reaction medium. More preferably, for organopolyphosphites in the first hydroformylation step (hydroformylation of the mixed C4 olefin stream), from 0.01 to 2 moles of organopolyphosphite ligand are employed per mole of metal with the second ligand being monodentate and present in excess relative to the metal center, preferably greater than 2 moles per mole of metal. Said amounts of organophosphorous ligand are the sum of both the amount of organophosphorous ligand that is bound (complexed) to the metal present and the amount of free (non-complexed) organophosphorous ligand present. Higher levels of the organopolyphosphites may be used in the second hydroformylation step (hydroformylation of C5 olefins) but are generally less than 5 moles of organopolyphosphite per mole metal. Since it is more preferred to produce non-optically active aldehydes by hydroformylating achiral olefins, the more preferred organophosphorous ligands are achiral type organophosphorous ligands, especially those encompassed by Formula (V) above, and more preferably those of Formulas (VI), (VII) and (VIII) above. If desired, make-up or additional organophosphorous ligand can be supplied to the reaction medium of the hydroformylation process at any time and in any suitable manner, e.g. to maintain a predetermined level of free ligand in the reaction medium.

As indicated above, the hydroformylation catalyst may be in heterogeneous form during the reaction and/or during the product separation. Such catalysts are particularly advantageous in the hydroformylation of olefins to produce high boiling or thermally sensitive aldehydes, so that the catalyst may be separated from the products by filtration or decantation at low temperatures. For example, the rhodium catalyst may be attached to a support so that the catalyst retains its solid form during both the hydroformylation and separation stages, or is soluble in a liquid reaction medium at high temperatures and then is precipitated on cooling.

As an illustration, the rhodium catalyst may be impregnated onto any solid support, such as inorganic oxides, (i.e. alumina, silica, titania, or zirconia) carbon, or ion exchange resins. The catalyst may be supported on, or intercalated inside the pores of, a zeolite, glass or clay; the catalyst may also be dissolved in a liquid film coating the pores of said zeolite or glass. Such zeolite-supported catalysts are particularly advantageous for producing one or more regioisomeric aldehydes in high selectivity, as determined by the pore size of the zeolite. The techniques for supporting catalysts on solids, such as incipient wetness, which will be known to those skilled in the art. The solid catalyst thus formed may still be complexed with one or more of the ligands defined above. Descriptions of such solid catalysts may be found in for example: *J. Mol. Cat.*, 1991, 70, 363-368; *Catal. Lett.*, 1991, 8, 209-214; *J. Organomet. Chem.*, 1991, 403, 221-227; *Nature*, 1989, 339, 454-455; *J. Catal.*, 1985, 96, 563-573; *J. Mol. Cat.*, 1987, 39, 243-259.

The metal, e.g., rhodium, catalyst may be attached to a thin film or membrane support, such as cellulose acetate or polyphenylenesulfone, as described in, for example, *J. Mol. Cat.*, 1990, 63, 213-221.

The metal, e.g., rhodium, catalyst may be attached to an insoluble polymeric support through an organophosphorus-containing ligand, such as a phosphite, incorporated into the polymer. The supported catalyst is not limited by the choice of polymer or phosphorus-containing species incorporated into it. Descriptions of polymer-supported catalysts may be found in for example: *J. Mol. Cat.*, 1993, 83, 17-35; *J. Am. Chem. Soc.*, 1987, 109, 7122-7127.

In the heterogeneous catalysts described above, the catalyst may remain in its heterogeneous form during the entire hydroformylation and catalyst separation process. In another embodiment of the invention, the catalyst may be supported on a polymer that, by the nature of its molecular weight, is soluble in the reaction medium at elevated temperatures, but precipitates upon cooling, thus facilitating catalyst separation from the reaction mixture. Such "soluble" polymer-supported catalysts are described in for example: *Polymer*, 1992, 33, 161; *J. Org. Chem.*, 1989, 54, 2726-2730.

More preferably, the reaction is carried out in the slurry phase due to the high boiling points of the products, and to avoid decomposition of the product aldehydes. The catalyst may then be separated from the product mixture, for example, by filtration or decantation. The reaction fluid may contain a heterogeneous metal-organophosphorous ligand complex catalyst, e.g., slurry, or at least a portion of the reaction fluid may contact a fixed heterogeneous metal-organophosphorous ligand complex catalyst during the hydroformylation process. In an embodiment of this invention, the metal-organophosphite ligand complex catalyst may be slurried in the reaction fluid.

In some particularly desirable embodiments, the first hydroformylation step (hydroformylation of mixed C4 olefin stream) employs two ligands, a bisphosphite as described above in formula <<V>> and a monodentate ligand as described in formulas <<I>> through <<IV>> and <<IX>>. The second hydroformylation step (hydroformylation of C5 olefins) may use the same catalyst system as the first hydroformylation step but preferably employs single ligand systems such as bisphosphite ligands of formula <<V>>, the triorganomonophosphites of formula <<IV>> or the triarylphosphines of formula <<IX>>.

In the first hydroformylation step in which two ligands are employed (e.g., a monodentate organophosphorous ligand and polydentate organophosphoshorous ligand such as a polyphosphite), the polyphosphite to rhodium mole ratio is below 2:1, preferably below 1:1, and most preferably below 0.9:1 but above 0.01:1 and most preferably above 0.1:1. The monodentate ligand is present in amounts such that the total polyphosphite and monodentate moles are in excess of the moles of rhodium and, in some embodiments, the monodentate ligand is used in molar excess (relative to rhodium) typically at least 1.1:1 and preferably greater than 5:1 (relative to rhodium) and greater than 50 mole % of the polyphosphite ligand. It should be understood that in such embodiments, monodentate ligand is intentionally added to the reaction fluid.

The variation in the linear branched ratio (herein also referred to as the "normal-to-iso ratio" or "N/I ratio") of the resulting C5 aldehydes from the hydroformylation step can be controlled by a number of factors. U.S. Pat. No. 7,863,487 teaches variations in the bisphosphite:rhodium ratio directly control the resulting N/I of the product of this first hydroformylation step. U.S. Pat. No. 8,741,173 teaches variation in the calixarene-based bisphosphite/triarylphosphine ratio can control the N/I. Additional control is possible by variations in the CO partial pressure in the reaction zone. Additionally, if multiple reactors in series are used such as in U.S. Pat. No. 7,615,645 and RU2561171, additional controls can be used such as olefin partition (WO2011/087696), syngas partial pressure partition (WO2011/087688), or rhodium partitioning (WO2011/087690) between the reactors.

The composition of the olefin feed can also be varied since 1-butene tends to give a higher valeraldehyde product ratio. Because most hydroformylation catalysts can also isomerize olefins, a pure 2-butene feed will still generate significant amounts of valeraldehyde presumably from initial isomerization of at least a portion of the 2-butene to 1-butene followed by hydroformylation. Techniques to effect the feed composition are well known (see, e.g., US Patent Publication No. 2010/0048959, EP080449, and CN106824282)

In the second and any subsequent hydroformylation steps (hydroformylation of C5 olefins, C6 olefins, C7 olefins, etc.), it is generally preferred to generate as high a linear: branched aldehyde ratio as possible such that the subsequent dehydration generates the alpha-olefin. In general, the polyphosphites and triarylphosphines generate higher N/I ratios than the monophosphites such that the polyphosphites and triarylphosphines are preferred.

When hydrolysable ligands are used for hydroformylation, the use of an aqueous buffer solution to prevent and/or lessen hydrolytic degradation of an organophosphite ligand and deactivation of a metal-organophosphite ligand complex is preferred as disclosed in U.S. Pat. No. 5,741,942. Aqueous buffers used in U.S. Pat. No. 5,741,944 are generally salts of weak acids or bases but are usually Group 1 or 2 metal (Na, K, Ca, etc.) salts of weak acids. In some cases where amines are used, they generate ionic salts, such as ammonium salts, when they neutralize and remove at least some amount of the phosphorus acidic compounds from the reaction fluid. The aqueous buffer solutions employable in this invention may comprise any suitable buffer mixture containing salts of oxyacids, the nature and proportions of which in the mixture are such that the pH of their aqueous solutions may range from 3 to 9, preferably from 4 to 8 and more preferably from 4.5 to 7.5. In this context suitable buffer systems may include mixtures of anions selected from the group consisting of phosphate, carbonate, citrate, maleate, fumarate, and borate compounds and cations selected from the group consisting of ammonium and alkali metals, e.g. sodium, potassium and the like. Such buffer systems and/or methods for their preparation are well known in the art.

Illustrative metal-organophosphorous ligand complex catalyzed hydroformylation processes that may experience hydrolytic degradation include those processes as described, for example, in U.S. Pat. Nos. 4,148,830; 4,593,127; 4,769, 498; 4,717,775; 4,774,361; 4,885,401; 5,264,616; 5,288, 918; 5,360,938; 5,364,950; 5,491,266 and 7,196,230. P—Z containing species that will likely undergo hydrolytic degradation include organophosphonites, phosphoramidites, fluorophosphonites, and the like, such as those described in WO 2008/071508, WO 2005/042458, and U.S. Pat. Nos. 5,710,344, 6,265,620, 6,440,891, 7,009,068, 7,145,042, 7,586,010, 7,674,937, and 7,872,156. These species will generate a variety of acidic and/or polar degradation products that can be extracted by use of the extractor technology taught in U.S. Pat. Nos. 5,744,649 and 5,741,944. Accordingly, the hydroformylation processing techniques that are advantageously employed with the invention disclosed herein may correspond to any known processing techniques. Preferred hydroformylation processes are those involving catalyst liquid recycle.

In one embodiment, processes of the present invention can include an extraction process for removing acidic impurities from a catalyst solution. Advantageously, the solution may be returned to a reaction zone of a hydroformylation process. The extraction process advantageously employs an aqueous buffer solution containing a metal salt of a weak oxyacid. The pH of this aqueous solution advantageously is in the range of 6-8 and the solution is capable of substantial buffering capacity within this range. The catalyst solution advantageously comprises an organophosphorous ligand and a metal-organophosphorous ligand complex, and the extraction process comprises the step of contacting the catalyst solution with an aqueous buffer solution within an extraction zone of the hydroformylation process. The extraction zone is located after the reaction zone. In one embodiment of the invention, a vaporizer follows the reaction zone to vaporize volatile components of the liquid effluent stream of the reaction zone. Any non-vaporized liquid is sent to the extraction zone. The aqueous buffer solution advantageously is used to stabilize (1) the organophosphorous ligand against hydrolytic degradation and (2) the metal-organophosphorous ligand complex against degradation or deactivation, and (3) to remove or reduce the ligand degradation products from the catalyst solution.

Examples of buffer systems include phosphate buffers or polycarboxylic acid salts (as disclosed in PCT Publication No. WO2013/184350), and the time of contact with the reaction fluid need only be that which is sufficient to neutralize at least some amount of the phosphorus acidic compounds that cause hydrolytic degradation of the desirable organophosphorous ligands. Preferably the amount of aqueous buffer solution is sufficient to at least maintain the concentration of such acidic compounds below the threshold level that causes substantial degradation of the hydrolyzable organophosphorous ligand. For instance, a preferred quantity of aqueous buffer solution is a quantity that ensures that any degradation of the organophosphorous ligand proceeds by the "non-catalytic mechanism" as described in "The Kinetic Rate Law for Autocatalytic Reactions" by Mata-Perez et al., *Journal of Chemical Education,* Vol. 64, No. 11, November 1987, pages 925 to 927, rather than by the "catalytic mechanism" described in said article. The amount of buffer correlates with buffer capacity or the amount of acid species that can be removed without significant change in the extraction fluid pH. The concentration of the unsaturated organic acid salt buffer is not narrowly critical. Advantageously, the concentration of the buffer salt in the buffer solution is from 0.001M to 0.8M and more preferably is from 0.01 to 0.04M. In one embodiment of the invention, the maximum aqueous buffer solution concentration is governed by practical considerations. The preparation of buffers is well known in the art. Advantageously, degassed ($O_2$-free) de-ionized water is employed in the preparation of the buffer solution. Mixtures of buffers may be employed. Alkoxylated amines or epoxides may also be used to remove acidic degradation products with the aid of an extractor as taught in PCT Publication Nos. WO2015/153070 and WO2014/051975.

The manner in which the metal-organophosphorous ligand complex catalyst containing reaction fluid and aqueous buffer solution are contacted, as well as the amount of aqueous buffer solution, temperature, pressure and contact time are not narrowly critical and need only be sufficient to obtain the results desired. For instance, said treatment may be carried out in any suitable vessel or container, e.g. any vessel suitable for use as a liquid/liquid extractor, that provides a suitable means for thorough contact between the reaction fluid and the aqueous buffer solution. In general, it is preferred to pass the reaction fluid through the aqueous buffer solution in a sieve tray extractor column in a countercurrent fashion. Such acid removal processes are preferably employed on each hydroformylation process or step incorporated into processes of the present invention if hydrolysable ligands are used in the respective reactors. Contacting conditions may vary greatly and any suitable combination of such conditions may be employed herein. For instance, a decrease in one condition may be compensated for by an increase in one or more of the other conditions, while the corollary is also true. In general, liquid temperatures ranging from 10° C. to 120° C., preferably from 20° C. to 80° C., and more preferably from 25° C. to 60° C., should be suitable for most instances, although lower or higher temperatures may be employed if desired. Advantageously, the treatment is carried out at pressures ranging from ambient to reaction pressure, and the contact time may vary from a matter of seconds or minutes to a few hours or more.

Success in removing phosphorus acidic compounds from the reaction fluid may be determined by measuring the rate of degradation (consumption) of the organophosphorous ligand present in the hydroformylation reaction medium. The consumption rate can vary over a wide range, e.g., from <0.6 up to 5 grams per liter per day, and will be governed by the best compromise between cost of ligand and treatment frequency to keep hydrolysis below autocatalytic levels. Preferably, the aqueous buffer solution treatment is carried out in such a manner that the consumption of the desired organophosphorous ligand present in the hydroformylation reaction medium is maintained at an acceptable rate, e.g., <0.5 grams of ligand per liter per day, and more preferably <0.1 grams of ligand per liter per day, and most preferably <0.06 grams of ligand per liter per day. As the neutralization and extraction of phosphorus acidic compounds into the aqueous buffer solution proceeds, the pH of the buffer solution will slowly decrease.

The removal of at least some amount of phosphorus acidic compounds, for example, $H_3PO_3$, $H_3PO_4$, aldehyde acids such as hydroxy alkyl phosphonic acids, such as hydroxyl butyl phosphonic acid, hydroxyl pentyl phosphonic acid, and the like, from the hydroformylation system allows one to control the acidity of the hydroformylation reaction medium, thereby stabilizing the useful organophosphorous ligand by preventing or lessening its hydrolytic decomposition. The need to control the acidity in organophosphorous promoted metal catalyzed hydroformylation is explained herein. Thus, the purpose of the buffer is to remove or reduce excessive acidity from the catalyst system in order to maintain a proper acidity level in the reaction fluid so that the consumption of the useful organophosphorous ligands do not hydrolytically degrade at an unacceptable rate while keeping catalyst activity at a productive level.

Optionally, an organic nitrogen compound may be added to the reaction fluid, e.g., hydroformylation reaction fluid, to scavenge the acidic hydrolysis by-products formed upon hydrolysis of the organophosphorous ligand, as taught, for example, in U.S. Pat. No. 4,567,306. Such organic nitrogen compounds may be used to react with and to neutralize the acidic compounds by forming conversion product salts therewith, thereby preventing the metal, e.g., rhodium, from complexing with the acidic hydrolysis by-products and thus helping to protect the activity of the metal, e.g., rhodium, catalyst while it is present in the reaction zone under reaction, e.g., hydroformylation, conditions. The choice of the organic nitrogen compound for this function is, in part, dictated by the desirability of using a basic material that is soluble in the reaction medium and does not tend to catalyze the formation of aldols and other condensation products at a significant rate or to unduly react with the product, e.g., aldehyde.

Another problem that has been observed when organophosphorous ligand promoted metal catalysts are employed in processes (e.g., continuous liquid catalyst recycle hydroformylation processes) that involve harsh conditions such as recovery of the aldehyde via a vaporizer-separator is, the slow loss in catalytic activity of the catalysts. This is believed to be due at least in part to the harsh conditions such as exist in a vaporizer employed in the separation and recovery of the aldehyde product from its reaction fluid. For instance, it has been found that when an organopolyphosphite promoted rhodium catalyst is placed under harsh conditions such as high temperature and low carbon monoxide partial pressure, the catalyst deactivates at an accelerated pace with time, due most likely to the formation of an inactive or less active rhodium species, which may also be susceptible to precipitation under prolonged exposure to such harsh conditions. Such evidence is also consistent with the view that the active catalyst, which under hydroformylation conditions is believed to comprise a complex of rhodium, organopolyphosphite, carbon monoxide and hydrogen, loses at least some of its coordinated carbon monoxide ligand during exposure to such harsh conditions as encountered in vaporization, which provides a route for the formation of catalytically inactive or less active rhodium species. The means for preventing or minimizing such catalyst deactivation and/or precipitation involves carrying out the invention described and taught in U.S. Pat. No. 5,731,472, which comprises carrying out the hydroformylation process under conditions of low carbon monoxide partial pressure in the presence of a free heterocyclic nitrogen compound as disclosed therein.

Other means to stabilize the hydroformylation catalysts particularly with monodentate hydrolysable organophosphorous ligands include the use of polymeric additives such as taught in U.S. Pat. No. 4,774,361 and PCT Publication No. WO2019/112866. Triarylphosphine-based catalysts are preferably stabilized using the amine additives taught in WO2011/419915.

Moreover, removal of the desired aldehyde product can cause concentrations of the other components of the reaction fluid to be increased proportionately. Thus, for example, the organophosphorous ligand concentration in the metal-organophosphorous ligand complex catalyst containing reaction fluid to be treated by the aqueous buffer in accordance with the process of this invention may range from between 0.005 and 15 weight percent based on the total weight of the reaction fluid. Preferably the ligand concentration is between 0.01 and 10 weight percent, and more preferably is between 0.05 and 5 weight percent on that basis. Similarly, the concentration of the metal in the metal-organophosphorous ligand complex catalyst containing reaction fluid to be treated by the aqueous buffer in accordance with the process of this invention may be as high as 5000 ppmw based on the weight of the reaction fluid. Preferably the metal concentration is between 50 and 2500 ppmw based on the weight of the reaction fluid, and more preferably is between 70 and 2000 ppmw.

Processes of the present invention include a second hydroformylation step for the hydroformylation of C5 olefins, and may include other hydroformylation steps (e.g., hydroformylation of C6 olefins, hydroformylation of C7 olefins, etc.). If the second or subsequent hydroformylation processes employ a monophosphite ligand, the use of polymeric ester stabilizers such as taught in U.S. Pat. No. 4,774,361 and PCT Publication No. WO2019/112866 are preferred. The use of a stripping gas vaporizer (such as described in U.S. Pat. No. 8,404,903) and a CO-enhanced stripping gas vaporizer (such as described in PCT Publication No. WO2016/08960) are also preferred.

If the second or subsequent hydroformylation processes employ a phosphine ligand, the use of a heterocyclic amine to stabilize the catalyst such as taught in PCT Publication No. WO2011/419915 is preferred. The harsh conditions needed to vaporize the product can lead to catalyst degradation even when the preferred stripping gas vaporizer is used (see U.S. Pat. No. 8,404,903).

The hydroformylation products may be asymmetric, non-asymmetric or a combination thereof, with the preferred products being non-asymmetric. The first, second, and any subsequent hydroformylation processes used in processes of the present invention may be conducted in any batch, continuous, or semi-continuous fashion, and may involve any catalyst liquid and/or gas recycle (such as described in U.S. Pat. Nos. 4,247,486 and 4,593,127) operation desired. Co-feed of the butene and pentene olefins or parallel trains for the first and second hydroformylation processes as taught in PCT Publication No. WO2015/094781 can be done to minimize capital costs.

The liquid recycle hydroformylation procedure (such as described in U.S. Pat. No. 4,148,830) generally involves withdrawing a portion of the liquid reaction medium containing the catalyst and aldehyde product from the hydroformylation reactor (or a reaction zone), either continuously or intermittently, and recovering the aldehyde product therefrom by use of a composite membrane, such as disclosed in U.S. Pat. Nos. 5,430,194 and 5,681,473, or by the more conventional and preferred method of distilling it, i.e. vaporization separation, in one or more stages under normal, reduced or elevated pressure, as appropriate, in a separate distillation zone. The non-volatilized metal catalyst containing residue can be recycled to the reaction zone as disclosed, for example, in U.S. Pat. No. 5,288,918. The use of the stripping gas vaporizer (such as disclosed in U.S. Pat. No. 8,404,903) is preferred in general, and for phosphite-based catalysts, the CO-enhanced stripping gas vaporizer (PCT Publication No. WO2016/08960) is preferred. Condensation of the volatilized materials, and separation and further recovery thereof, e.g., by further distillation, can be carried out in any conventional manner The crude aldehyde product can be passed on for further purification and isomer separation, if desired, and any recovered reactants (e.g., olefinic starting material and syngas) can be recycled in any desired manner to the reaction zone (reactor). The recovered metal catalyst containing raffinate of such membrane separation or recovered non-volatilized metal catalyst containing residue of such vaporization separation can be recycled, to the reaction zone (reactor) in any conventional manner desired.

In some embodiments, the hydroformylation reaction fluid employable herein includes any fluid derived from any corresponding hydroformylation process that contains at least some amount of four different main ingredients or components, i.e., the aldehyde product, a metal-organophosphorous ligand complex catalyst, free organophosphorous ligand and an organic solubilizing agent for said catalyst and said free ligand, said ingredients corresponding to those employed and/or produced by the hydroformylation process from whence the hydroformylation reaction mixture starting material may be derived. The hydroformylation reaction mixture compositions employable herein can and normally will contain minor amounts of additional ingredients such as those that have either been deliberately employed in the hydroformylation process or formed in situ during said process. Examples of such ingredients that can also be present include unreacted olefin starting material, carbon monoxide and hydrogen gases, and in situ formed type products, such as saturated hydrocarbons and/or unreacted isomerized olefins corresponding to the olefin starting materials, ligand degradation compounds, and high boiling liquid aldehyde condensation by-products, as well as other inert co-solvent type materials or hydrocarbon additives, if employed.

The reaction conditions of the hydroformylation processes used in processes of the present invention may include any suitable hydroformylation conditions heretofore employed for producing optically active and/or non-optically active aldehydes. For instance, the total gas pressure of hydrogen, carbon monoxide and olefin starting compound of the hydroformylation processes may range from 1 to 69,000 kPa. In general, however, it is preferred that the hydroformylation processes be operated at a total gas pressure of hydrogen, carbon monoxide and olefin starting compound of less than 14,000 kPa and more preferably less than 3,400 kPa. The minimum total pressure is limited predominantly by the amount of reactants necessary to obtain a desired rate of reaction. More specifically the carbon monoxide partial pressure of the hydroformylation processes used in processes of the present invention is preferably from 1 to 6,900 kPa, and more preferably from 21 to 5,500 kPa, while the hydrogen partial pressure is preferably from 34 to 3,400 kPa and more preferably from 69 to 2,100 kPa. In general, $H_2$:CO molar ratio of gaseous hydrogen to carbon monoxide in a reaction zone may range from 1:10 to 100:1 or higher, the more preferred hydrogen to carbon monoxide molar ratio being from 1:10 to 10:1.

In general, the hydroformylation processes may be conducted at any operable reaction temperature. Advantageously, the hydroformylation processes are conducted at a reaction temperature from $-25°$ C. to $200°$ C. In general, hydroformylation reaction temperatures of $50°$ C. to $120°$ C. are preferred for all types of olefinic starting materials. It is to be understood that when non-optically active aldehyde products are desired, achiral type olefin starting materials and organophosphorous ligands are employed and when optically active aldehyde products are desired prochiral or chiral type olefin starting materials and organophosphorous ligands are employed. The hydroformylation reaction conditions employed will be governed by the type of aldehyde product desired.

The hydroformylation processes used in processes of the present invention may be carried out using one or more suitable reactors such as, for example, a fixed bed reactor, a fluid bed reactor, a tubular reactor, a venturi reactor, a bubble column reactor, a continuous stirred tank reactor (CSTR) or a slurry reactor. The optimum size and shape of the reactor will depend on the type of reactor used. In general, for fluid bed reactors, a small, spherical catalyst particle is preferred for easy fluidization. With fixed bed reactors, larger catalyst particles are preferred so the back pressure within the reactor is kept reasonably low. The at least one reaction zone employed may be a single vessel or may comprise two or more discrete vessels. The at least one separation zone employed in the hydroformylation processes may be a single vessel or may comprise two or more discrete vessels. The at least one buffer treatment zone if employed the hydroformylation processes used in the present invention may be a single vessel or may comprise two or more discreet vessels. The reaction zone(s) and separation zone(s) employed herein may exist in the same vessel or in different vessels. For example, reactive separation techniques such as reactive distillation, reactive membrane separation and the like may occur in the reaction zone(s).

The hydroformylation processes used in processes of the present invention can be conducted in a batch or continuous fashion, with recycle of unconsumed starting materials if required. Each hydroformylation reaction process can be conducted in a single reaction zone or in a plurality of reaction zones, in series or in parallel or it may be conducted batchwise or continuously in an elongated tubular zone or series of such zones. The materials of construction employed should be substantially inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the process especially to maintain the desired molar ratio of the starting materials. The reaction steps may be effected by the incremental addition of one of the starting materials to the other. Also, the reaction steps can be combined by the joint addition of the starting materials. The starting materials may be added to each or all the reaction zones in series. When complete conversion is not desired or not obtainable, the starting materials can be separated from the product, for example by distillation, and the starting materials then recycled back into the reaction zone.

The hydroformylation processes may be conducted in either glass lined, stainless steel or similar type reaction equipment. The reaction zone(s) may be fitted with one or more internal and/or external heat exchanger(s) in order to control undue temperature fluctuations, or to prevent any possible "runaway" reaction temperatures.

The hydroformylation processes used in embodiments of the present invention may be conducted in one or more steps or stages. The exact number of reaction steps or stages will be governed by the best compromise between capital costs and achieving high catalyst selectivity, activity, lifetime and ease of operability, as well as the intrinsic reactivity of the starting materials in question and the stability of the starting materials and the desired reaction product to the reaction conditions.

In an embodiment, the hydroformylation may be carried out in a multistaged reactor such as described, for example, in U.S. Pat. No. 5,728,893. Such multistaged reactors can be designed with internal, physical barriers that create more than one theoretical reactive stage per vessel. In effect, it is like having a number of reactors inside a single continuous stirred tank reactor vessel. Multiple reactive stages within a single vessel is a cost effective way of using the reactor vessel volume. It significantly reduces the number of vessels that otherwise would be required to achieve the same results. Fewer vessels reduces the overall capital required and maintenance concerns with separate vessels and agitators. The first and subsequent hydroformylation steps can be done in the same reactor or reaction zones (i.e., in a co-feed operation) or as a dual train sharing a common vaporizer as described in PCT Publication No. WO2015/094781.

One key feature of some embodiments of the present invention is to adjust the ratio of linear (e.g., valeraldehyde) and branched (e.g. 2-methylbutraldehyde) C5 aldehydes produced from the mixed C4 olefin stream using first hydroformylation process. The adjustment of this ratio can control the relative amounts of isoprene and mono-olefins having at least six carbon atoms produced using the downstream steps in processes of the present invention. In some embodiments, for example, the ratio of linear and branched C5 aldehydes produced in the first hydroformylation process can be adjusted to match a target ratio of isoprene and C6 olefins produced in subsequent steps.

The ratio of linear to branched C5 aldehydes produced in the hydroformylation process can be adjusted in a number of ways. For example, the ratio of linear to branched C5 aldehydes in the mixture of step (a) is increased by increasing the ratio of polydentate organophosphorus ligand to rhodium in at least one reaction zone. This is described, for example, in U.S. Pat. No. 7,863,487. Similarly, U.S. Pat. No. 8,741,173 teaches variation in the calixarene-based bisphosphite/triarylphosphine can control the N/I ratio.

Additional control is possible by variations in the CO partial pressure in the reactor/reaction zone.

Additionally, if multiple reactors in series are used, additional controls can be used such as adjusting the syngas partial pressure, adjusting the mixed C4 olefin partial pressure, and/or adjusting the transition metal (e.g., rhodium) concentration between the reactors.

For example, in some embodiments, the ratio of linear to branched C5 aldehydes can be increased by decreasing the synthesis gas partial pressure. Such approaches are described further in PCT Publication No. WO2011/087688.

In some embodiments, the ratio of linear to branched C5 aldehydes in the mixture of step (a) is increased by increasing the mixed C4 olefin partial pressure in the first reaction zone. In some further embodiments, the mixed C4 olefin partial pressure in the first reaction zone can be changed by one or more of the following: (1) increasing the temperature in the first reaction zone; (2) reducing the amount of mixed C4 olefin provided to a subsequent reaction zone; and/or (3) changing the olefin feed rate to the first reaction zone. Such approaches are described further in PCT Publication No. WO2011/087696.

In some embodiments, the ratio of linear to branched C5 aldehydes in the mixture of step (a) is increased by increasing the transition metal concentration in at least one reaction zone. In some further embodiments, the transition metal concentration in a first reaction zone may be changed by one or more of the following: (1) partitioning catalyst recycle from a product separation zone between a first reaction zone and one or more subsequent reaction zones; or (2) adding transition metal without any ligand either as a transition metal precursor or a metal-organomonodentate compound; or (3) decreasing the transition metal concentration in the first reaction zone by removing up to 20% of the transition metal catalyst from the reaction system into a separate vessel; or (4) returning transition metal catalyst previously removed (as in option (3)) to the first reaction zone. Such approaches are described further in PCT Publication No. WO2011/087690.

An alternative means to change the ratio of valeraldehyde to branched C5 aldehydes is to adjust or change the composition of the incoming mixed C4 olefin stream. Higher 2-butene content in the mixed C4 olefin stream will tend to generate more 2-methylbutyraldehyde and isobutene will form mostly 3-methylbutyraldehyde; the converse is also true. One means to adjust the composition of the mixed C4 olefin stream is to change the amount of any recycled olefin recovered after a product-catalyst separation step in the hydroformylation process as the recycled olefin is often be higher in 2-butene content than conventional mixed C4 feeds.

Any one of the above process variables can be readily used to shift the balance of the linear to branched aldehyde to match the needs of the isoprene and C6+ olefin production units. Of course, more than one can be used simultaneously and many are cumulative in their effect.

As indicated above, it is generally preferred to carry out the hydroformylation processes used in embodiments of processes of the present invention in a continuous manner In general, continuous hydroformylation processes are well known in the art and may involve: (a) hydroformylating the olefinic starting material(s) with carbon monoxide and hydrogen in a liquid homogeneous reaction mixture comprising a solvent, the metal-organophosphorous ligand complex catalyst, and free organophosphorous ligand; (b) maintaining reaction temperature and pressure conditions favorable to the hydroformylation of the olefinic starting material(s); (c) supplying make-up quantities of the olefinic starting material(s), carbon monoxide and hydrogen to the reaction medium as those reactants are used up; and (d) recovering the desired aldehyde hydroformylation product(s) in any manner desired. The continuous process can be carried out in a single pass mode, i.e., wherein a vaporous mixture comprising unreacted olefinic starting material(s) and vaporized aldehyde product is removed from the liquid reaction mixture from whence the aldehyde product is recovered and make-up olefinic starting material(s), carbon monoxide and hydrogen are supplied to the liquid reaction medium for the next single pass through without recycling the unreacted olefinic starting material(s). Such types of recycle procedure are well known in the art and may involve the liquid recycling of the metal-organophosphorous complex catalyst fluid separated from the desired aldehyde reaction product(s), such as disclosed, for example, in U.S. Pat. No. 4,148,830 or a gas recycle procedure such as disclosed, for example, in U.S. Pat. No. 4,247,486, as well as a combination of both a liquid and gas recycle procedure if desired. The most preferred hydroformylation process of this invention comprises a continuous liquid catalyst recycle process. Suitable liquid catalyst recycle procedures are disclosed, for example, in U.S. Pat. Nos. 4,668,651; 4,774,361; 5,102,505 and 5,110,990.

The aldehyde product mixtures from the hydroformylation processes may be separated from the other components of the crude reaction mixtures in which the aldehyde mixtures are produced by any suitable method known to those of ordinary skill in the art based on the teachings herein in order to provide a crude aldehyde stream. Suitable separation methods include, for example, solvent extraction, crystallization, distillation, vaporization, wiped film evaporation, falling film evaporation, phase separation, filtration and the like or any combination thereof. It may be desired to remove the aldehyde products from the crude reaction mixture as they are formed through the use of trapping agents as described in PCT Publication No. WO 88/08835. One method for separating the aldehyde mixtures from the other components of the crude reaction mixtures is by membrane separation. Such membrane separation can be achieved as set out in U.S. Pat. Nos. 5,430,194 and 5,681,473. Other recovery techniques are disclosed in U.S. Pat. Nos. 4,148,830 and 4,247,486. For instance, in a continuous liquid catalyst recycle process the portion of the liquid reaction mixture (containing aldehyde product, catalyst, etc.), i.e., reaction fluid, removed from the reaction zone can be passed to a separation zone, e.g., vaporizer/separator, wherein the desired aldehyde product can be separated via distillation, in one or more stages, under normal, reduced or elevated pressure, from the liquid reaction fluid, condensed and collected in a product receiver, and further purified if desired. The remaining non-volatilized catalyst containing liquid reaction mixture may then be recycled back to the reactor as may if desired any other volatile materials, e.g., unreacted olefin, together with any hydrogen and carbon monoxide dissolved in the liquid reaction after separation thereof from the condensed aldehyde product, e.g., by distillation in any conventional manner In general, it is preferred to separate the desired aldehydes from the catalyst-containing reaction mixture under reduced pressure and at low temperatures so as to avoid possible degradation of the organophosphorous ligand and reaction products. When an alpha-mono-olefin reactant is also employed, the aldehyde derivative thereof can also be separated by the above methods.

More particularly, distillation and separation of the desired aldehyde product from the metal-organophosphorous complex catalyst containing reaction fluid may take place at any suitable temperature desired. In general, it is preferred that such distillation take place at relatively low temperatures, such as below 150° C., and more preferably at a temperature in the range of from 50° C. to 140° C. It is also generally preferred that such aldehyde distillation take place under reduced pressure, e.g., a total gas pressure that is substantially lower than the total gas pressure employed during hydroformylation when low boiling aldehydes (e.g., $C_4$ to $C_6$) are involved or under vacuum when high boiling aldehydes (e.g. $C_7$ or greater) are involved. For instance, a common practice is to subject the liquid reaction product medium removed from the hydroformylation reactor to a pressure reduction so as to volatilize a substantial portion of the unreacted gases dissolved in the liquid medium that now contains a much lower synthesis gas concentration than is present in the reaction medium to the distillation zone, e.g. vaporizer/separator, wherein the desired aldehyde product is distilled. In general, distillation pressures ranging from vacuum pressures on up to total gas pressure of 340 kPa should be sufficient for most purposes.

The use of a stripping gas vaporizer (as described for example in U.S. Pat. No. 8,404,903) is preferred, and especially with catalysts containing hydrolysable ligands, the CO-enhanced stripping gas vaporizer (as described for example in PCT Publication No. WO2016/08960) is preferred.

After the hydroformylation of the mixed C4 olefin stream in processes of the present invention, the crude mixed C5 aldehydes are separated from the catalyst solution as described above. The resulting material may comprise mixtures of valeraldehyde, 2-methylbutyraldehyde, and 3-methylbutyraldehyde. The latter is produced from the isobutene in the mixed C4 olefin stream. The mixture may also comprise other components such as unreacted butenes, other olefins, syngas, water, inert gases (e.g., N2), and the like.

The low-boiling non-aldehyde components may be removed in a forecolumn operation. Alternatively, the stream is sent directly to an aldehyde separation process typically a distillation system where the branched aldehydes and the valeraldehyde comprise separate product streams.

Due to the close boiling points of the 2-methylbutyraldehyde ("2MeBal"; BP=91° C.) and 3-methylbutyraldehyde ("3MeBAL"; BP=92° C.), it is not practical to separate these aldehydes. Thus, it is preferable in some embodiments to control the amount of isobutene in the mixed C4 olefin feed to control the amount of 3MeBAL in the product. Alternatively, 3MeBAL may be converted to isoprene as well using techniques such as described in U.S. Pat. No. 4,560,822.

The resulting branched C5 aldehydes stream is subjected to a dehydration process to directly produce isoprene. That is, 2-methylbutyraldehyde (2MBAL) in the C5 aldehydes stream can be dehydrated to produce isoprene using techniques known those of ordinary skill in the art based on the teachings herein. For example, Journal of Catalysis (1999), 188(2), 291-299 describes the synthesis of isoprene via dehydration of 2-methylbutanal on boron and aluminum phosphate catalysts. Examples of suitable catalysts for the dehydration of 2-methylbutanal are given in U.S. Pat. Nos. 547,614, 4,587,372, 4,665,266, 4,734,538, EP 80449, EP 219042, GB 2227250, EP 272662, and Applied Catalysis (1986), 28(1-2), 161-8. The reaction is shown generally as:

A linear valeraldehyde product stream is then treated with hydrogen in the presence of a hydrogenation catalyst to form the corresponding alcohol. Such reductions are well known in the art and typically involve supported Group VI-VIII transition metals either in vapor or liquid phase processes. Examples of such processes include those described in U.S. Pat. Nos. 4,762,817, 4,876,402, 4,960,960, 5,093,535, and 6,765,119 and European Patent Publication No. 0 008 767.

While the concentration of hydrogen in the reaction zone is not critical, there generally should be an excess of hydrogen over the stoichiometric requirement relative to the aldehyde to be hydrogenated. Generally, the mol ratio of hydrogen to aldehyde will be from about 5 to 400 and preferably from about 10 to 200. For aldehydes containing from about 2 to 8 carbon atoms, the mol ratio of hydrogen to aldehyde preferably is in the range of about 10 to 30.

The resulting pentanol stream may contain small amounts of branched alcohols if branched aldehyde was present; these compounds may be removed by distillation at this stage or preferably fed into the next process without further purification. Esters, hemi-acetals, and ethers may also be present in the crude stream and can be removed if desired.

The dehydration of alcohols to the corresponding olefin is known to those of having ordinary skill in the art (e.g., as described in PCT Publication No. WO2004078336). The process preferably maximizes the formation of the linear (terminal) olefin while minimizing the formation of ethers and isomerized olefins. Typically a heterogeneous catalyst is used at elevated temperature and a substantial recycle of unreacted alcohol and ether byproducts is used to effect high overall conversion of the alcohol to the corresponding olefin. For example, $Al_2O_3$, silicon dioxide, titanium dioxide and zirconium dioxide are commonly used low acidity catalysts. Promoted alumina catalysts such as CaO- or $Ca_2O_3$-containing catalyst are preferred. Typical temperatures range from above 200° C. up to 400° C. (typically between 250 and 350° C.) at pressures of 1 to 30 atmospheres, typically between 2 and 10 atmospheres. The second dehydration catalyst converting pentanol to 1-pentene and the third or subsequent dehydration catalysts converting C6 and higher alcohols to the corresponding olefins may be the same or different for each alcohol. Additionally, in some embodiments, each of the alcohols can be fed to a single dehydration catalyst (as a "co-feed" operation) and the resulting olefins separated afterwards.

The resulting initial crude 1-pentene is typically refined to remove and optionally recycle unreacted alcohol, hemi-acetals, and ethers using techniques known to those having ordinary skill in the art.

The resulting 1-pentene stream is then subjected to a second hydroformylation process. Typically this is done in a separate hydroformylation zone compared to the first hydroformylation since in this case, it is generally preferred to generate as high a linear: branched (N/I) ratio as possible. If the end-product C6 alcohol can have higher branching, then a co-feed process with the initial mixed C4 butene stream or an integrated dual train process such as described in PCT Publication No. WO2015/094781 can be employed in some embodiments.

The product/catalyst separation considerations at this stage are analogous to the product/catalyst separation at the first hydroformylation step (hydroformylation of the mixed C4 olefin stream).

With polyphosphites and even polyphosphines, the hydroformylation process may generate a sufficiently high linear:branched (N/I) ratio that an aldehyde separation process is not needed after product/catalyst separation. However, any contained CO should be removed prior to being introduced into the subsequent hydrogenation zone as CO is typically a potent hydrogenation catalyst inhibitor.

The resulting hexanal stream is then treated with hydrogen in the presence of a hydrogenation catalyst to form the hexanol product stream. Such reductions are well known in the art and typically involve supported Group VI-VIII transition metals either in vapor or liquid phase processes as described above in connection with hydrogenation of the pentanal stream.

The resulting hexanol material may contain branched alcohols if branched aldehyde was present which may be removed by distillation at this stage or preferably fed into the next process without further purification. Esters, hemi-acetals, and ethers may also be present in the crude stream which can be removed and/or recycled if desired. Alternatively, all or part of the stream may be refined to generate a high purity 1-hexanol product for the dehydration step described herein or a portion of this refined stream may be removed for other applications such as surfactants, plasticizers, and the like.

Generally speaking the same process and/or catalyst that was used for the 1-pentanol dehydration can be used to dehydrate the 1-hexanol stream. A co-feed process can be used if downstream refining systems are capable of the separations (see, e.g., PCT Publication Nos. WO2003/024910 and WO2010/138435). Preferably, this process is done in a separate dehydration unit to simplify downstream refining and recycle processes.

The resulting 1-hexene is suitable for use as a polyolefins co-monomer, or other applications, and optionally can be reprocessed again as described in PCT Publication No. WO2003/024910 to generate higher linear olefins as the market demands For example, the hydroformylation-hydrogenation-dehydration processes can be done in block campaigns to convert 1-pentene to 1-hexene (stored in a temporary storage tank until fed back into the process in the next block operation), then repeated to form 1-heptene and so on.

Isoprene generated from the branched C5 aldehyde process is a useful rubber precursor as well as in other applications. The 1-hexene and higher olefins are useful as polyolefin comonomers as well as in other applications. The ability to vary the ratio of these two different products simply by controlling the hydroformylation of the inexpensive mixed butene supply offers an economically advantaged process.

What is claimed is:

1. A process for preparing isoprene and mono-olefins comprising at least six carbon atoms, the process comprising:
   (a) hydroformylating a mixed C4 olefin stream, wherein the mixed C4 olefin stream comprises 1-butene, 2-butene, and optionally isobutene, with a hydroformylation catalyst, wherein the hydroformylation catalyst comprises rhodium with monodentate organophosphorous ligand and optionally polydentate organophosphorous ligand, to produce a mixture comprising linear and branched C5 aldehydes;
   (b) separating the branched C5 aldehydes from the linear C5 aldehydes to provide a branched C5 aldehyde stream and a linear C5 aldehyde stream;
   (c) dehydrating the branched C5 aldehydes in the branched C5 aldehyde stream using a dehydration catalyst to form a stream comprising isoprene;
   (d) hydrogenating the linear C5 aldehydes in the linear C5 aldehyde stream to form a C5 alcohol stream;

(e) dehydrating the C5 alcohols in the C5 alcohol stream with a second dehydration catalyst to form a C5 olefin stream;

(f) hydroformylating the C5 olefins in the C5 olefin stream to generate a C6 aldehyde stream;

(g) hydrogenating the C6 aldehydes in the C6 aldehyde stream to form a C6 alcohol stream; and (h) dehydrating the C6 alcohols in the C6 alcohol stream with a third dehydration catalyst to form a C6 olefin stream.

2. The process of claim 1, wherein the ratio of linear and branched C5 aldehydes produced in step (a) is adjusted to match a target ratio of isoprenes and C6 olefins in steps (c) and (h), respectively.

3. The process of claim 2, wherein the hydroformylation catalyst comprises a polydentate organophosphorous ligand, and the ratio of polydentate organophosphorous ligand to rhodium is less than 1:1.

4. The process of claim 3, wherein the hydroformylation in step (a) is conducted in one more reaction zones, and wherein the ratio of linear to branched C5 aldehydes in the mixture of step (a) is increased by increasing the ratio of polydentate organophosphorus ligand to rhodium in at least one reaction zone.

5. The process of claim 2, wherein the hydroformylation in step (a) comprises contacting the mixed C4 olefin stream with synthesis gas and the hydroformylation catalyst, the contacting conducted at hydroformylation conditions comprising a synthesis gas partial pressure, and wherein the ratio of linear to branched C5 aldehydes in the mixture of step (a) is increased by decreasing the synthesis gas partial pressure.

6. The process of claim 2, wherein the hydroformylation in step (a) comprises contacting the mixed C4 olefin stream with synthesis gas and the hydroformylation catalyst, the contacting conducted in first and subsequent reaction zones and at hydroformylation conditions comprising a mixed C4 olefin partial pressure, wherein the ratio of linear to branched C5 aldehydes in the mixture of step (a) is increased by increasing the mixed C4 olefin partial pressure in the first reaction zone.

7. The process of claim 2, wherein the hydroformylation in step (a) is conducted in one or more reaction zones, and wherein the ratio of linear to branched C5 aldehydes in the mixture of step (a) is increased by increasing the transition metal concentration in at least one reaction zone.

8. The process of claim 1, wherein the C5 olefin stream further comprises C5 alcohols and ethers, and further comprising separating the C5 alcohols and ethers from the C5 olefin stream and returning the separated C5 alcohols and ethers to dehydration step (e).

9. The process of claim 1, wherein the hydroformylation in step (f) is conducted in the same reactor or plurality of reactors as the hydroformylation in step (a).

10. The process of claim 1, wherein the target ratio of isoprene from step (c) relative to C6 olefin produced from step (h) is from 1:1 to 1:50.

11. The process of claim 1, wherein the C5 olefin stream comprises linear C5 alpha olefins, linear C5 internal olefins, and branched C5 olefins.

12. The process of claim 1, further comprising adjusting the composition of the mixed C4 olefin stream prior to step (a).

13. The process of claim 1, further comprising:

(i) hydroformylating the C6 olefins in the C6 olefin stream to generate a C7 aldehyde stream;

(j) hydrogenating the C7 aldehydes in the C7 aldehyde stream to form a C7 alcohol stream; and (k) dehydrating the C7 alcohols in the C7 alcohol stream with a fourth dehydration catalyst to form a C7 olefin stream.

14. The process of claim 13 further comprising:

(l) hydroformylating the C7 olefins in the C7 olefin stream to generate a C8 aldehyde stream;

(m) hydrogenating the C8 aldehydes in the C8 aldehyde stream to form a C8 alcohol stream; and (n) dehydrating the C8 alcohols in the C8 alcohol stream with a fifth dehydration catalyst to form a C8 olefin stream.

15. The process of claim 1, wherein the monodentate organophosphphorous ligand is a monophosphite, and wherein the hydroformylation catalyst further comprises polydentate organophosphorous ligand, and wherein the polydentate organophosphorous ligand is a bisphosphite.

* * * * *